United States Patent [19]

Oinuma et al.

[11] Patent Number: 4,977,165

[45] Date of Patent: * Dec. 11, 1990

[54] PIPERIDINE DERIVATIVE AND THERAPEUTIC AND PREVENTIVE AGENTS FOR ARRHYTHMIA CONTAINING SAME

[75] Inventors: Hitoshi Oinuma, Tsukuba; Motosuke Yamanaka, Abiko; Kazutoshi Miyake, Ushiku; Tomonori Hoshiko, Ibaraki; Norio Minami, Tsukuba; Tadao Shoji, Ibaraki, all of Japan

[73] Assignee: Eisai Co., Ltd., Tokyo, Japan

[*] Notice: The portion of the term of this patent subsequent to Oct. 31, 2006 has been disclaimed.

[21] Appl. No.: 234,468

[22] Filed: Aug. 19, 1988

[30] Foreign Application Priority Data

Aug. 24, 1987 [JP] Japan .................. 62-209726
Aug. 24, 1987 [JP] Japan .................. 62-209727
Aug. 24, 1987 [JP] Japan .................. 62-209728

[51] Int. Cl.$^5$ .................. A61K 31/445; C07D 211/96
[52] U.S. Cl. .................. 514/318; 514/331; 514/327; 514/821; 546/194; 546/216; 546/230; 546/232
[58] Field of Search .................. 546/194, 216, 230, 232, 546/286, 288, 300, 296; 514/318, 331, 821, 605, 327; 564/99

[56] References Cited

U.S. PATENT DOCUMENTS

| | | | |
|---|---|---|---|
| 3,341,584 | 9/1967 | Larsen et al. | 564/99 |
| 3,968,242 | 7/1976 | Gallo et al. | 514/605 |
| 4,044,150 | 8/1977 | Kreighbaum et al. | 514/605 |
| 4,544,654 | 10/1985 | Davey et al. | 514/210 |
| 4,666,935 | 5/1987 | Stout et al. | 514/318 |
| 4,876,262 | 10/1989 | Oinuma et al. | 546/230 |

FOREIGN PATENT DOCUMENTS 0158775 10/1985 European Pat. Off. ......... 514/210

*Primary Examiner*—Glennon H. Hollrah
*Assistant Examiner*—Mark W. Russell
*Attorney, Agent, or Firm*—Flynn, Thiel, Boutell & Tanis

[57] ABSTRACT

A piperidine compound has the generic formula and is useful to treat arrhythmia.

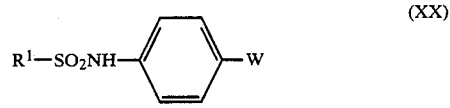

in which $R^1$ is a lower alkyl and W is:

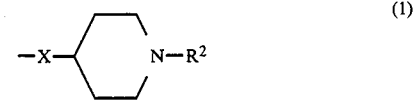

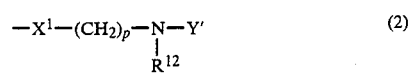

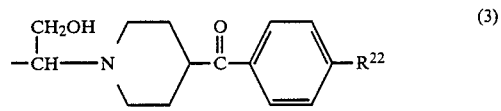

X is —S—, —SO— or —SO$_2$—, $R^2$ is hydrogen or —(CH$_2$)$_n$—Y, n is an integer of 1 to 5, Y is an aryl, pyridyl or a substituted pyridyl, X' is —CO— or —CH(OH)—, p is an integer of 1 to 4, $R^{12}$ is hydrogen or a lower alkyl, Y' is —(CH$_2$)$_m$—A, m is 1 or 2, A is an aryl, a substituted aryl, pyridyl or a substituted pyridyl, $R^{12}$ and Y may form a 5- or 6-membered ring or a 5- or 6-membered ring having one or more substituents and $R^{22}$ is hydrogen, a halogen, a lower alkyl, a lower alkoxy or hydroxy.

20 Claims, No Drawings

PIPERIDINE DERIVATIVE AND THERAPEUTIC AND PREVENTIVE AGENTS FOR ARRHYTHMIA CONTAINING SAME

TECHNICAL FIELD

The present invention relates to piperidine derivatives and pharmacologically acceptable salts thereof having an excellent medicinal effect, a process for producing same and medicines containing same.

PRIOR ART

Arrhythmia is induced by cardiac diseases such as myocardial infarction and heart failure. In a serious case, ventricular fibrillation is provoked to cause a sudden death.

Though various antiarrhythmic agents are now available on the market, none of them can give satisfactory effect and safety at the same time. For example, antiarrhythmic agents of Class I according to the Vaughan-Williams classification have only an insufficient effect of preventing the ventricular fibrillation and are problematic in that they restrain the myocardia and induce arrhythmia by inhibiting the conduction. Although β-blockers and calcium antagonists are also used, they exhibit their effects with only limited certainty though the safety is higher than that of the antiarrhythmic agents of Class I.

On the other hand, antiarrhythmic agents of Class III (effective in prolonging the duration of action potential) do not restrain the myocardia and scarcely inhibit the conduction in the heart in view of the mechanism of the action. Therefore, occurrence of arrhythmia induced by them is thought to be scarce. The development of antiarrhythmic agents of Class III is thus expected.

OBJECTS OF THE INVENTION

An object of the present invention is to provide new piperidine derivatives and pharmacologically acceptable salts thereof. Another object of the invention is to provide a process for producing these derivatives and salts. Still another object of the invention is to provide medicines containing any of these derivatives and salts as the active ingredient.

The invention provides a new piperidine compound having the generic formula (XX) and a pharmacologically acceptable salt thereof:

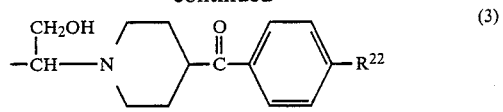
(XX)

in which $R^1$ is a lower alkyl and W is:

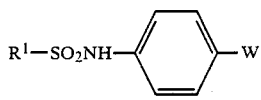
(1)

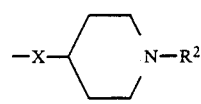
(2)

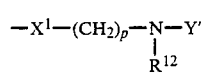
(3)

X is —S—, —SO— or —SO$^2$—, $R^2$ is hydrogen or —(CH$^2$)n-Y, n is an integer of 1 to 5, Y is an aryl, pyridyl or a substituted pyridyl, X' is —CO— or —CH(OH)—, p is an integer of 1 to 4, $R^{12}$ is hydrogen or a lower alkyl, Y' is —(CH2)m—A, m is 1 or 2, A is an aryl, a substituted aryl, pyridyl or a substituted pyridyl, $R^{12}$ and Y may form a 5- or 6-membered ring or a 5- or 6-membered ring having one or more substituents and $R^{22}$ is hydrogen, a halogen, a lower alkyl, a lower alkoxy or hydroxy.

The compound of the invention includes three embodiments having the formula (XX) in which W is (1), (2) and (3), respectively. The compound in which W is (1) is preferable and the compound in which W is (1) and X is —SO— is most preferable.

The invention also provides a pharmaceutical composition which comprises a pharmacologically effective amount of the compound as defined above or a pharmacologically acceptable salt thereof and a pharmacologically acceptable carrier and then a therapeutic or preventive medicament for arrhythmia which comprises the compound as defined above or a pharmacologically acceptable salt thereof.

The invention provides a method of treating a patient afflicted with arrythmia which comprises administering to the patient a therapeutically effective amount of the compound as defined above.

The pharmacologically acceptable salts include inorganic acid addition salts such as hydrochloride, sulfate, hydrobromide, perchlorate and hydroiodide as well as organic acid addition salts such as oxalate, maleate, fumarate, succinate and methanesulfonate.

The intended compounds (XX) and pharmacologically acceptable salts of the present invention having an excellent antiarrhythmic activity and a high safety are usable as antiarrythmic agents. Their effects on particular arrhythmia on which other medicines are ineffective and intractable arrhythmia can be expected.

It is expected, therefore, that the compounds of the present invention are usable for the treatment and prevention of all types of arrhythmia (supraventricular) arrhythmia as the antiarrhythmic agents of the Class III. These compounds are usable for controlling recurrent arrhythmia of human beings and also for preventing sudden death induced by ventricular fibrillation.

When the compound of the present invention is to be used as the antiarrhythmic agent, it is given by oral administration or parenteral administration (intramuscular or subcutaneous administration). The dose is not particularly limited and it varies depending on the type of the disease, symptoms, age, conditions and body weight of the patient, another treatment conducted simultaneously with this treatment, if any, frequency of the treatment and the quality of to adults by oral administration, the dose is about 1 to 100 mg, preferably about 5 to 50 mg and particularly about 5 to 15 mg a day. It is given once or more times a day. When it is given by injection, the dose is about 0.01 to 1 mg/kg, preferably about 0.03 to 0.1 mg/kg.

The antiarrhythmic agent is in the form of, for example, powders, fine grains, granules, tablets, capsules, suppositories or injections. In the formulation, an ordinary carrier is used and an ordinary preparation method is employed.

An oral solid preparation is prepared by adding an excipient and, if necessary, a binder, disintegrator, lubricant, colorant, corrigent, etc. to the active ingredient and shaping the mixture into tablets, coated tablets, granules, powder or capsules by an ordinary method.

The excipients include, for example, lactose, corn starch, white sugar, glucose, sorbitol, crystalline cellulose and silicon dioxide. The binders include, for example, polyvinyl alcohol, polyvinyl ether, ethylcellulose, methylcellulose, acacia, tragacanth, gelatin, shellac, hydroxypropylcellulose, hydroxypropylstarch and polyvinylpyrrolidone. The disintegrators include, for example, starch, agar, gelatin powder, crystalline cellulose, calcium carbonate, sodium hydrogencarbonate, calcium citrate, dextrin and pectin. The lubricants include, for example, magnesium stearate, talc, polyethylene glycol, silica and hardened vegetable oils. The colorants include those accepted as colorants for medicines. The corrigents include, for example, cocoa powder, menthol, aromatic powder. These tablets and granules can be suitably coated with sugar, gelatin, etc.

In the preparation of the injection, additives such as a pH ajusting agent, buffering agent, stabilizer or solubilizer are added, if necessary, to the active ingredient and an intravenous injection is prepared therefrom by an ordinary method.

The invention will be explained in more detail below in reference to the compounds (1) (2) and (3).

Compound in which W is (1)

The embodiment (1) of the compound of the invention has the generic formula (1-I).

$$R^1-SO_2NH-\phantom{X}-X-\phantom{N}N-R^2 \qquad (1\text{-}I)$$

wherein $R^1$ represents a lower alkyl group, X represents a group of the formula: —S—, $$-\overset{O}{\underset{}{\overset{\uparrow}{S}}}-$$

or $$-\overset{O}{\underset{\underset{O}{\parallel}}{\overset{\parallel}{S}}}-$$

and R represents a hydrogen atom or a group of the formula: —$(CH_2)_n$—Y in which n is an integer of 1 to 5 and Y is an aryl group or a substituted or unsubstituted pyridyl group.

In the definition of the compounds of the present invention, the lower alkyl groups $R^1$ include straight chain or branched alkyl groups having 1 to 6 carbon atoms, such as methyl, ethyl, n-propyl, n-butyl, isopropyl, isobutyl, 1-methylpropyl, tert-butyl, n-pentyl, 1-ethylpropyl, isoamyl and n-hexyl groups, among which a methyl group is the most desirable.

X represents a group of the formula: —S—, $$-\overset{O}{\underset{}{\overset{\uparrow}{S}}}- \text{ or } -\overset{O}{\underset{\underset{O}{\parallel}}{\overset{\parallel}{S}}}-.$$

In the definition of $R^2$, n is an integer of 1 to 5, preferably 1 or 2.

In the definition of Y, the aryl group is preferably a phenyl group. The phenyl group may be substituted with the above-described lower alkyl groups having 1 to 6 carbon atoms, lower alkoxy groups derived from these lower alkyl groups or halogen atoms. The phenyl group may be substituted with 1 to 3 substituents which may be either the same or different from one another. Therefore, preferred examples of the aryl groups include substituted or unsubstituted phenethyl and benzyl groups. When Y is a pyridyl group, it is represented by the formula:

$$\phantom{X}-R^3$$

wherein $R^3$ represents a hydrogen atom, a lower alkyl, lower alkoxy, cyano or hydroxyl group or a halogen atom. The most desirable examples of $R^2$ include a pyridylmethyl group, a pyridylethyl group and groups in which the pyridine ring is substituted with a methyl group such as methylpyridylmethyl and methylpyridylethyl groups.

Compound in which W is (2)

The embodiment (2) of the compound of the invention has the generic formula (2-I).

$$R^1-SO_2NH-\phantom{X}-X'-(CH_2)_p-\underset{R^{12}}{\overset{}{N}}-Y' \qquad (2\text{-}I)$$

wherein $R^1$ represents a lower alkyl group, $X'$ represents a group of the formula:

$$-\overset{O}{\overset{\parallel}{C}}- \text{ or } -\overset{OH}{\underset{}{\overset{\mid}{CH}}}-,$$

p represents an integer of 1 to 4, $R^{12}$ represents a hydrogen atom or a lower alkyl group, $Y'$ represents a group of the formula: —$(CH_2)_m$—A in which m is an integer of 1 or 2 and A is a substituted or unsubstituted aryl group or pyridyl group, or $R^{12}$ and $Y'$ may form together a five- or six-membered ring which may be substituted.

In the definition of $R^1$ and $R^{12}$, the lower alkyl groups are straight-chain or branched ones having 1 to 6 carbon atoms, such as methyl, ethyl, n-propyl, n-butyl, isopropyl, isobutyl, 1-methylpropyl, tert-butyl, n-pentyl, 1-ethylpropyl, isoamyl and n-hexyl groups.

$R^1$ is most preferably a methyl group and $R^{12}$ is most preferably a methyl or ethyl group.

In the definition of A, the aryl group is most preferably a substituted or unsubstituted phenyl group.

The substituents include, for example, the above-mentioned lower alkyl groups having 1 to 6 carbon atoms, lower alkoxy groups derived from these lower alkyl groups and halogen atoms. The phenyl group may be thus substituted with 1 to 3 substituents which may be either the same or different from one another.

The substituted pyridyl groups are those of the formula:

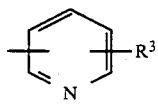

wherein $R^3$ represents a lower alkyl, lower alkoxy or cyano group or a halogen atom.

The most desirable example of the substituted pyridyl groups is a methylpyridyl group.

$R^{12}$ and $Y'$ may form together a five- or six-membered ring which may be substituted. The rings include pyrrole and piperidine rings. The most desirable example of them is a group of the formula:

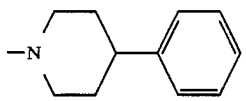

Compound in which W is (3)

The embodiment (3) of the compound of the invention has the generic formula (3-I).

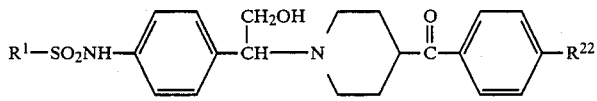

wherein $R^1$ represents a lower alkyl group and $R^{22}$ represents a hydrogen or halogen atom or a lower alkyl, lower alkoxy or hydroxyl group.

In the definition of $R^1$ and $R^{22}$ in the general formula (3I), the lower alkyl groups are straight-chain or branched ones having 1 to 6 carbon atoms, such as methyl, ethyl, n-propyl, n-butyl, isopropyl, isobutyl, 1-methylpropyl, tert-butyl, n-pentyl, 1-ethylpropyl, isoamyl and n-hexyl groups. The lower alkoxy groups in the definition of $R^{22}$ include all of lower alkoxy groups derived from the above-mentioned lower alkyl groups. The most desirable groups $R^1$ and $R^{22}$ are methyl and ethyl groups, and methoxy and ethoxy groups, respectively.

The halogen atoms in the definition of $R^{22}$ include chlorine, bromine, iodine and fluorine atoms.

Methods for preparing the compounds of the invention are described below in reference to the compounds (1), (2) and (3).

The compounds (I) of the present invention can be prepared by various processes. Typical examples of them are given below.

In the following processes, not only the final step of forming the intended product but also preceding steps involving the starting compounds are also described in order to facilitate the understanding.

Preparation process A

When X is a group of the formula, —S—:

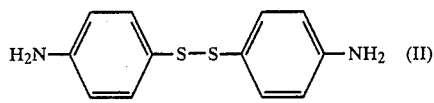

the first step | alkylsulfonylation

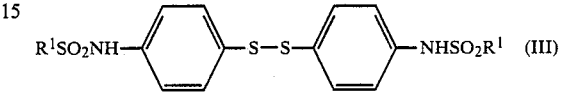

the second step | reduction

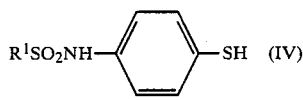

the third step

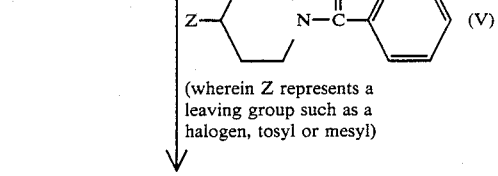

(wherein Z represents a leaving group such as a halogen, tosyl or mesyl)

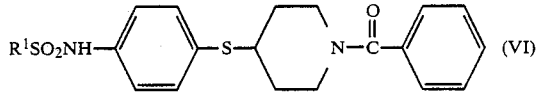

(3-I) the fourth step | hydrolysis

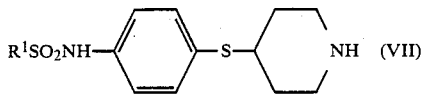

the fifth step | alkylation
Z—(CH$_2$)$_n$—Y (VIII)
(wherein Z, Y and n are as defined above)

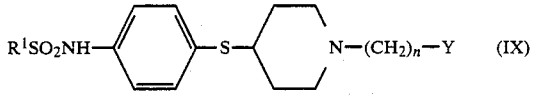

The first step

In this step, alkylsulfonyl groups are introduced into the aniline derivative (II).

The aniline derivative (II) is reacted with an alkylsulfonylating agent such as an alkylsulfonyl chloride or alkylsulfonic anhydride in the presence of a base such as pyridine or triethylamine in an inert solvent such as DMF, acetonitrile, benzene, dichloromethane, chloroform, tetrahydrofuran or dioxane at a temperature of −20° C. to room temperature in an ordinary manner to prepare an alkylsulfonyl anilide (III).

The second step

In this step, the S—S bond of the alkylsulfonylanilide derivative (III) obtained in the first step is reductively broken.

The bond breakage can be effected by reduction conducted with a combination of a metal such as zinc or tin with an acid, with lithium aluminum hydride or sodium borohydride, or in a mixture of triphenylphosphine with a hydrous alcohol or hydrous dioxane in an ordinary manner. Preferably the thiol derivative (IV) is obtained by conducting the reaction in the presence of triphenylphosphine or EDTA as well as acidic hydrous methanol or 1N HCl in hydrous methanol or hydrous dioxane at a temperature in the range of 0° C. to a reflux temperature.

The third step

In this step, the thiol derivative (IV) obtained in the second step is coupled with the piperidine derivative (V).

The thiol derivative (IV) is alkylated with the piperidine derivative (V) in the presence of a base such as sodium hydrogencarbonate, potassium carbonate, pyridine or triethylamine in an inert solvent such as DMF, DMSO, acetonitrile, benzene, dioxane or tetrahydrofuran at a temperature in the range of room temperature to 100° C. to prepare a corresponding sulfide derivative (VI).

The fourth step

In this step, the amido group of the sulfide derivative (VI) obtained in the third step is hydrolyzed.

This reaction is conducted in, for example, a dilute aqueous alkali solution or dilute aqueous mineral acid solution. In a preferred example, the hydrolysis is conducted in 2 to 6 N hydrochloric acid or 0.5 to 3 N aqueous sodium hydroxide solution at a temperature in the range of room temperature to a reflux temperature to prepare the amine derivative (VII).

The fifth step (1) N-Alkylation of the compound (VII) of the above formula (I) wherein n is 0 and Y is H:

The compound (VII) obtained in the fourth step is subjected to the condensation reaction with the compound (VIII) in an ordinary manner.

In a preferred process, the reaction is conducted in the presence of a deacidifying agent, such as potassium carbonate or sodium carbonate, and potassium iodide, which is unnecessary when Z is iodine, in a solvent such as N,N-dimethylformamide, dimethyl sulfoxide, acetonitrile, acetone, butanol, propanol, ethanol or methanol at a temperature of about 50° to 120° C. to prepare the compound (IX).

(2) When n is 2 and Y is a group of the formula:

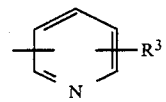

wherein $R^3$ is as defined above, in the definition $R^2$, the intended compound can be prepared also by a process described below.

Namely, the above reaction scheme can be represented more specifically as follows for facilitating the understanding:

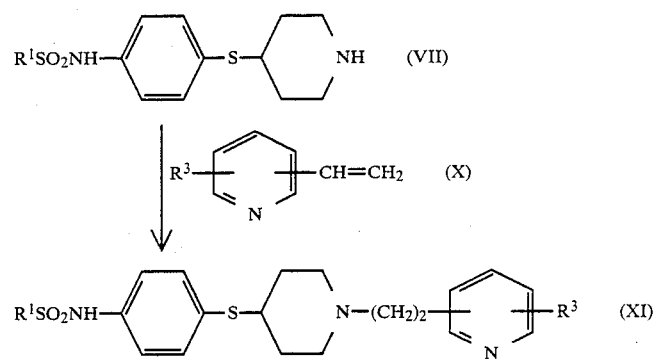

The unsubstituted or substituted vinylpyridine (X) is reacted with the compound (free base) (VIII) obtained in the above-described fourth step or a pharmacologically acceptable acid addition salt thereof in a lower alkyl alcohol such as methanol, ethanol or propanol alone or a mixture thereof with water at a temperature in the range of room temperature to about 100° C. to prepare the intended compound (XI). When a free base is used as the starting material, preferred results are obtained by using an acidic catalyst such as acetic acid or hydrochloric acid or an alkali metal catalyst such as sodium.

Preparation process B

When X represents a group of the formula,

Process (1)

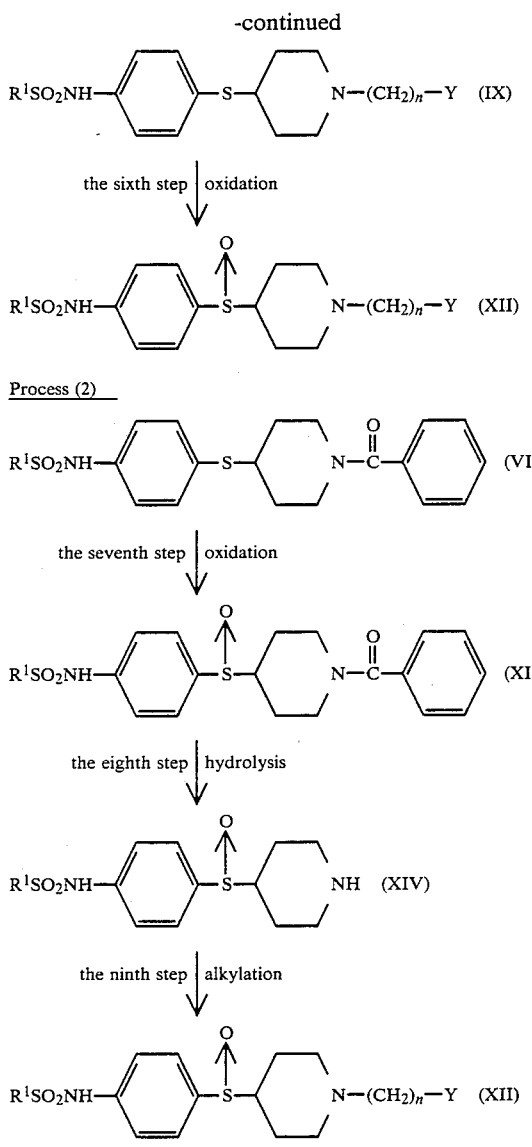

Process (2)

The sixth step

In this step, the sulfide derivative (IX) obtained in the fifth step is oxidized into the sulfoxide derivative (XII).

The oxidation is conducted in an ordinary manner. For example, the compound (IX) is oxidized with an oxidizing agent such as sodium periodate, hydrogen peroxide, peracetic acid or m-chloroperbenzoic acid in the presence of an excess mineral acid such as hydrochloric acid in a solvent such as methanol, ethanol, 2-propanol or water. Preferably the reaction is conducted in the presence of excess hydrochloric acid in hydrous methanol at a temperature in the range of 0° C. to room temperature.

The seventh step

In this step, the sulfide derivative (VI) obtained in the third step is oxidized to give a sulfoxide derivative (XIII).

The intended product (XIII) can be prepared in the same manner as that of the sixth step. In this case, no excess acid is necessitated.

The eighth step

The compound (XIII) obtained in the seventh step is hydrolyzed. The intended compound (XIV) of the present invention can be obtained by, for example, the same process as that of the fourth step.

The ninth step

The compound (XIV) obtained in the eighth step is alkylated. The intended compound (XII) of the present invention can be obtained by, for example, the same process as that of the fifth step.

Preparation process C

When X represents a group of the formula,

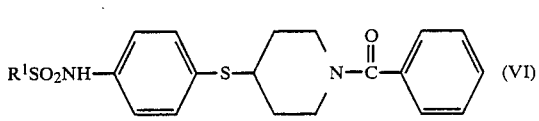

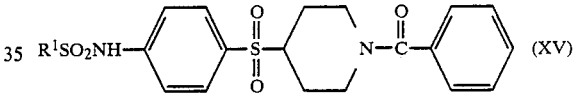

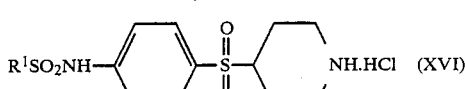

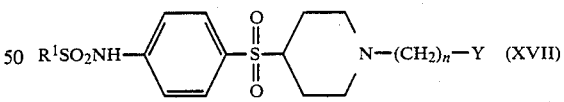

The tenth step

In this step, the sulfide derivative (VI) obtained in the third step is oxidized to give the sulfone derivative (XV).

The reaction is conducted by using an oxidizing agent such as hydrogen peroxide, a peracid, e.g. peracetic acid or m-chlorobenzoic acid, or sodium periodate in a solvent such as methanol, ethanol, propanol, dichloromethane or chloroform at a temperature in the range of room temperature to a reflux temperature. Preferably the reaction is conducted in the presence of at least two equivalents of m-chlorobenzoic acid in chloroform or dichloromethane at 0° C. to room temperature.

The eleventh step

In this step, the acryl group of the sulfone derivative (XV) obtained in the tenth step is hydrolyzed to give the amine derivative (XVI).

The intended compound (XVI) of the present invention can be obtained by, for example, the same process as that of the fourth step.

The twelfth step

In this step, the amine derivative (XVI) obtained in the eleventh step is N-alkylated. The intended compound (XVII) of the present invention can be obtained by, for example, the same process as that of the fifth step.

The piperidine derivatives obtained by the present invention are capable of curing arrhythmia by prolonging the refractory period by specifically prolonging the duration of the action potential without exerting any influence on the conduction rate of the heart muscles. They correspond to the antiarrythmic agents of Class III of the above-mentioned Vaughan-Williams classification.

Preparation of Compound (2)

The compounds (I) of the present invention can be prepared by various processes. Typical examples of them are given below.

Preparation process A

When X is a group of the formula,

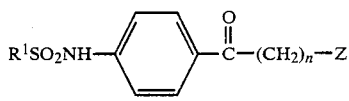

wherein Z represents a leaving group such as a halogen atom, a methanesulfonyloxy or p-toluenesulfonyloxy group

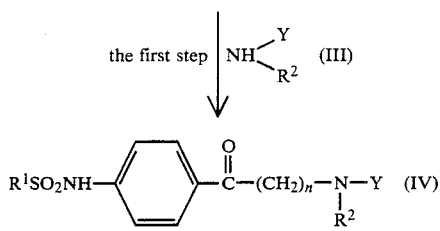

Preparation process B

When n in the formula (I) is 2 or 3, the intended compound can be prepared also by the following process:

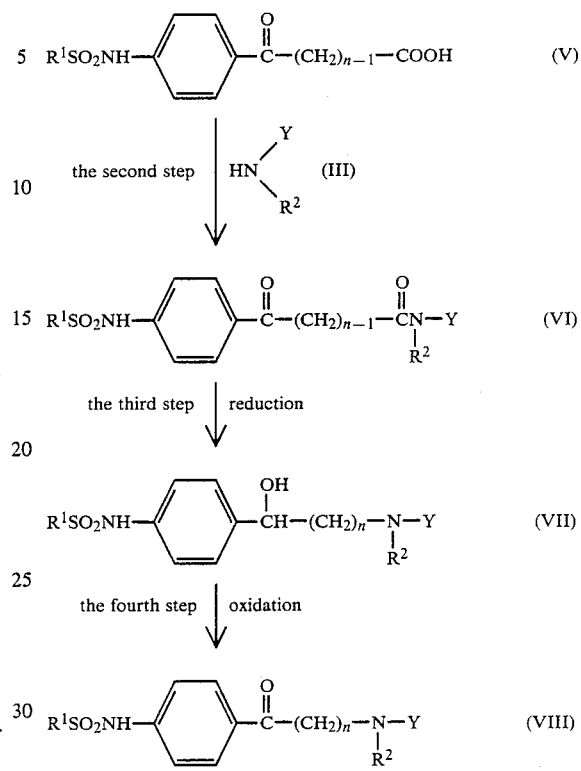

Preparation process C

When $R^2$ in the formula (I) is not hydrogen but a lower alkyl group, the compound can be prepared also by the following process:

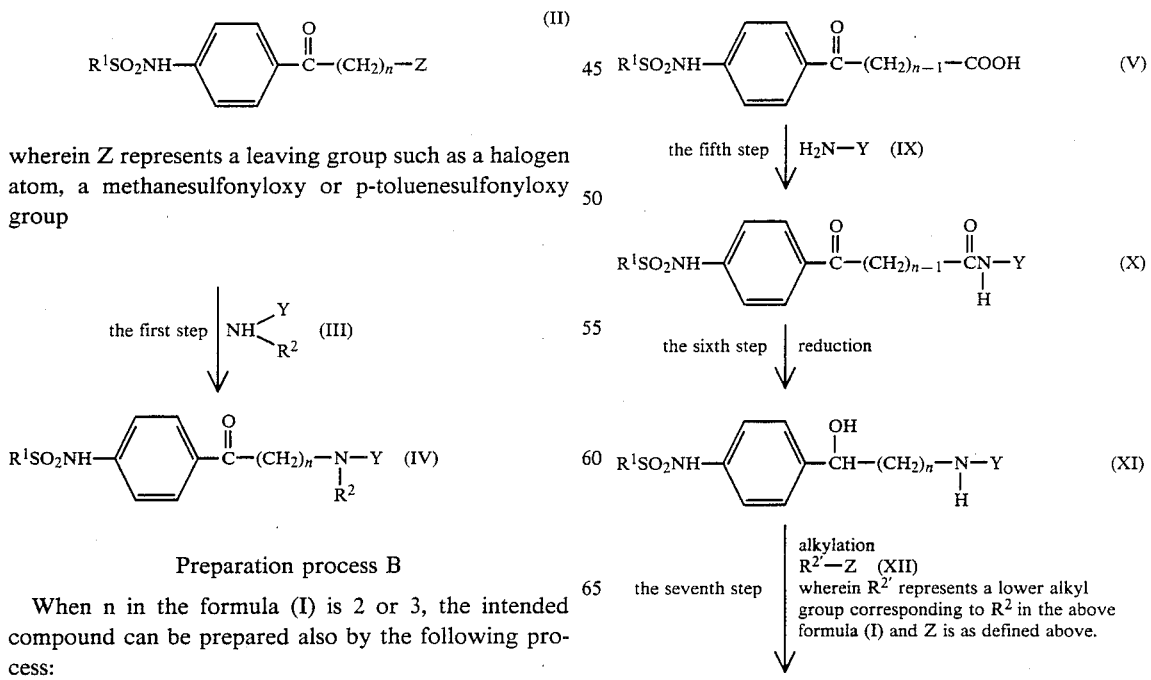

-continued

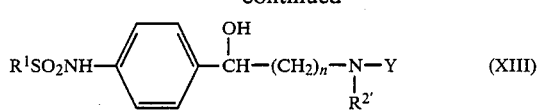

the eighth step | oxidation

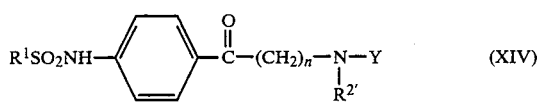

The first step

In this step, a known benzoyl derivative (II) or that prepared by a known process is reacted with a known amine derivative (III) or that prepared by a known process to obtain an amine derivative (IV) of the present invention.

The benzoyl derivative (II) is reacted with the amine derivative (III) in the presence of a base in a solvent such as dimethylformamide, dimethyl sulfoxide, a lower alkyl alcohol, e.g. methanol, ethanol or propanol, or acetone at a reaction temperature of about 50° to 120° C. in an ordinary manner to give an intended compound (IV). The bases include, for example, potassium carbonate, sodium carbonate, sodium bicarbonate, sodium ethoxide, sodium methoxide and sodium hydride.

The second step

In this step, a known carboxylic acid derivative (V) or that prepared by a known process in subjected to a condensation reaction with the amine derivative (III) to give an amide derivative (VI).

An active derivative derived from the carboxylic acid derivative (V), such as an acid halide, acid anhydride, mixed acid anhydride, imidazolid [prepared from the carboxylic acid derivative (V) and 1,1'-carbonyldiimidazole] or active ester [prepared from, for example, the carboxylic acid derivative (V), dicyclohexylcarbodiimide and 1-hydroxybenzotriazole] is reacted with a suitable amine derivative (III) in an ordinary manner.

The third step

In this step, the amine derivative (VI) obtained in the second step is reduced to give an amine derivative (VII).

The reduction is conducted in an ordinary manner. Preferably the amide derivative (VI) is reduced with a reducing agent such as lithium aluminum hydride or diborane in an inert solvent such as tetrahydrofuran, dioxane or ether at a temperature in the range of room temperature to the reflux temperature.

The fourth step

In this step, the amine derivative (VIII) obtained in the third step is oxidized with a suitable oxidizing agent to give an intended compound (VIII) of the present invention.

The oxidation is conducted preferably with a chromic acid reagent such as Jones reagent or Collins reagent, Swan oxidizing agent (oxaloyl chloride and dimethyl sulfoxide), dicyclohexylcarbodiimide or diethyl azadicarboxylate.

The fifth step

In this step, the carboxylic acid derivative (V) is condensed with a known primary amine derivative (IX) or that prepared by a known process to give an amide derivative (X). The reaction is conducted, for example, in the same manner as that of the second step.

The sixth step

The reaction is conducted in the same manner as that of the third step.

The seventh step

In this step, the amine derivative (XI) obtained in the sixth step is N-alkylated to give an amine derivative (XIII).

For example, the compound (XI) is reacted with a compound of the above formula (XII) having a leaving group such as a halogen in the presence of a base in a solvent such as dimethylformamide, dimethyl sulfoxide, methanol, ethanol or propanol at a reaction temperature of about 50° to 120° C. in an ordinary manner to give the intended compound (XIII). The bases usable in this step include, for example, potassium carbonate, sodium carbonate, sodium hydrogencarbonate, sodium ethoxide, sodium methoxide and sodium hydride.

The eighth step

In this step, the amine derivative (XIII) obtained in the seventh step is oxidized to give an intended benzoyl derivative (XIV) of the present invention.

The reaction is conducted, for example, in the same manner as that of the fourth step. The piperidine derivatives obtained by the present invention are capable of curing arrhythmia by prolonging the refractory period by specifically prolonging the duration of the action potential without exerting any influence on the conduction rate of the heart muscles. They correspond to the antiarrythmic agents of Class III of the above-mentioned Vaughan-Williams classification.

Preparation of Compound (3)

The compounds (I) of the present invention can be prepared by various processes A typical example of them is given below.

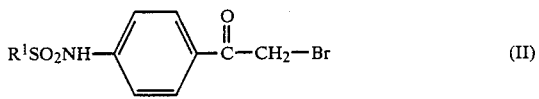

the first step | reduction

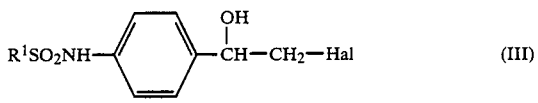

wherein Hal represents a halogen atom the second step | alkylation.

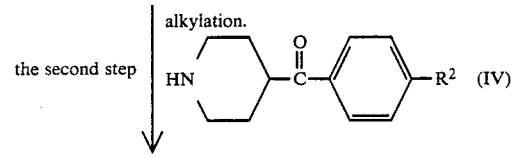

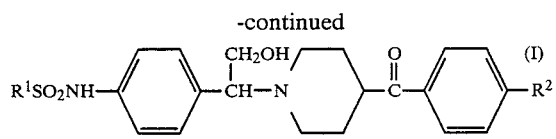

The first step

In this step, a known ketone derivative (II) is reduced to obtain a corresponding alcohol derivative (III).

The ketone derivative (II) is reduced with a reducing agent such as sodium borohydride or sodium cyanoborohydride in a solvent such as methanol, ethanol or propanol at a temperature of −b 20° C. to room temperature in an ordinary manner to give the compound (III).

The second step

In this step, the halide (III) such as bromide obtained in the first step is reacted with a known piperidine derivative (IV) or that prepared by a known process to give the intended aminoalkylated compound (I) of the present invention.

For example, the compound (IV) is reacted with the halide (III) in the presence of a base in a solvent such as dimethylformamide, dimethyl sulfoxide, a lower alkyl alcohol such as methanol, ethanol or propanol, or acetone at a reaction temperature of about 50° to 120° C. in an ordinary manner to give the intended compound (I). The bases include, for example, potassium carbonate, sodium carbonate, sodium hydrogencarbonate, sodium ethoxide, sodium methoxide and sodium hydride.

The piperidine derivatives obtained by the present invention are capable of curing arrhythmia by prolonging the refractory period by specifically prolonging the duration of action potential without exerting any influence on the conduction rate of the heart muscles. They correspond to the antiarrythmic agents of Class III of the above-mentioned Vaughan-Williams classification.

EXMPERMENTAL EXAMPLE 1

Effects of the action potential duration in the isolated myocardium of guinea-pigs Right ventricular papillary muscles were isolated from male guinea-pigs of Hartley strain weighing 300 to 400 g and fixed at the bottom of an acrylic bath with pins. They were perfused with Tyrode solution kept at 37° C. and saturated with a mixture of 95% $O_2$ and 5% $CO_2$. The muscles were stimulated at 1 Hz with rectangular pulses of 1 msec duration and supramaximal voltage. Action potentials were recorded using conventional glass microelectrodes filled with 3M KCl. The duration of the action potential and the maximum velocity of the upstroke of the action potential (Vmax) were determined. Each of the test compounds was included in Tyrode solution at $10^{-6}$ or $10^{-5}$ M and perfused. The effects of the $10^{-6}$M solution was observed for the first 10 min, then those of the $10^{-5}$M solution were observed for another 10 min.

The results are shown in Tale 1. The test compounds shown in Example 1 were as follows. Sotalol, a beta-adrenoceptor antagonist was employed as the reference drug because this compound is known to prolong the duration of the myocardial action potential.

Test on the compound (1) and results

Compound A: 4-(4-methylsulfonylaminophenylthio)-1-[2-(3-pyridyl)ethyl]piperidine

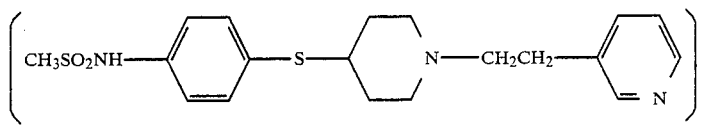

Compound B: 4-(4-methylsulfonylaminophenylsulfinyl)-1-[2-(3-pyridyl)ethyl]piperidine

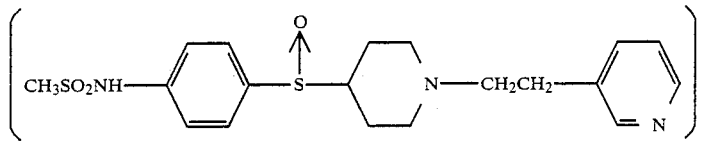

It is apparent from the results of the above-described experiments that the compounds of the present invention have an excellent antiarrhythmic effects.

Acute toxicity tests of typical compounds (the above-mentioned compounds A and B) of the present invention were conducted by applying them to male ddy mice weighing 20 to 30 g by intravenous injection. They showed an $LD_{50}$ of 180 to 400 mg/kg.

Test on the compound (2) and results

Compound A: Compound prepared in Example 1:
N-[4-{N-methyl-(6-methyl-2-pyridyl)ethylamino}-acetylphenyl]methanesulfonamide dioxalate:

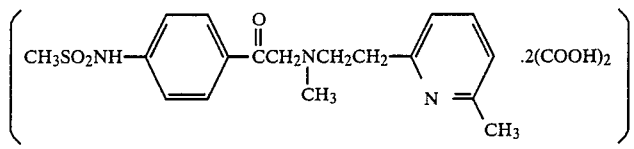

Compound B: Compound prepared in Example 2:
N-[4-[3-{N-methyl-(6-methyl-2-pyridyl)-ethylamino}propionyl]phenyl]methanesulfonamide dioxalate:

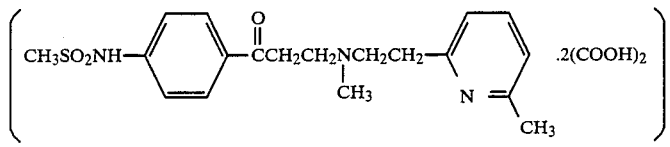

Compound C: Compound prepared in Example 4:
N-[4-[4-{N-methyl-2-(6-methyl-2-pyridyl)ethylamino}butyryl]phenyl]methanesulfonamide dioxalate:

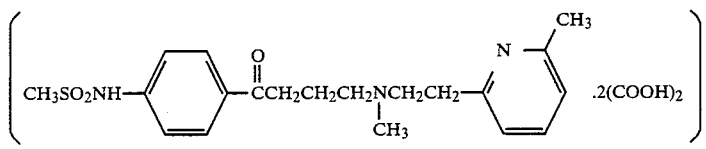

Compound D: Compound prepared in Example 5:
N-[4-{N-ethyl-2-(6-methyl-2-pyridyl)ethylamino}butyryl]phenyl]methanesulfonamide dioxalate:

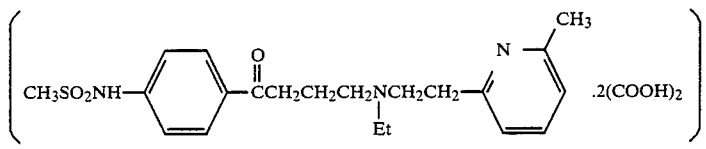

Compound E: Compound prepared in Example 6:
N-[4-[5-{6-methyl-2-pyridyl)ethylamino}valeryl]phenyl]methanesulfonamide dioxalate:

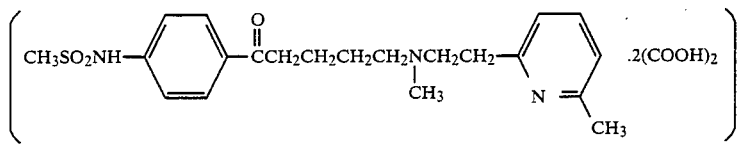

It is apparent from the results of the above-described experiments that the compounds of the present invention have excellent antiarrhythmic effects.

Acute toxicity tests of typical compounds (the above-mentioned compounds A to E) of the present invention were conducted by applying them to male ddy mice weighing 20 to 30 g by intravenous injection. They showed an $LD_{50}$ of 180 to 400 mg/kg.

Test on the compound (3) and results

Compound A: Compound prepared in Example 1:
N-[4-[2-hydroxy-1-{4-(4-fluorobenzoyl)piperidyl}ethyl]phenyl]methanesulfonamide hydrochloride

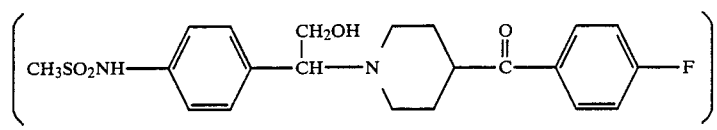

Compound B: Compound prepared in Example 4:
N-[4-[2-hydroxy-1-{4-(4-chlorobenzoyl) piperidyl}ethyl]phenyl]methanesulfonamide

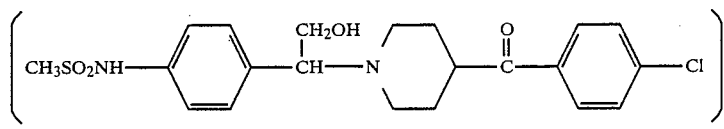

It is apparent from the results of the above-described experiments that the compounds of the present invention have excellent antiarrhythmic effects.

Acute toxicity tests of typical compounds (the above-mentioned compounds A and B) of the present invention were conducted by applying them to male ddy mice weighing 20 to 30 g by intravenous injection. They showed an $LD_{50}$ of 180 to 400 mg/kg.

Results are shown below in terms of $APD_{90}$ prolongation (%) and $V_{max}$ inhibition (%).

TABLE 1

| test | $10^{-6}$ M | | $10^{-5}$ M | |
|---|---|---|---|---|
| compound | $APD_{90}$ | $V_{max}$ | $APD_{90}$ | $V_{max}$ |
| compound (1) | | | | |
| A | 11 | 0 | 20 | 0 |
| B | 14 | 0 | 40 | 0 |
| compound (2) | | | | |
| A | 12 | 0 | 16 | 0 |
| B | 18 | 0 | 19 | 0 |
| C | 17 | 0 | 31 | 0 |
| D | 17 | 0 | 31 | 0 |
| E | 14 | 0 | 27 | 0 |
| compound (3) | | | | |
| A | 16 | 0 | 25 | 0 |
| B | 13 | 0 | 11 | 0 |
| Sotalol | 0 | 0 | 7 | 0 |

The invention will be illustrated below in reference to examples. They are disclosed on the compounds (1), (2) and (3).

Compound (1)

Example 1

(1) Preparation of N-benzoyl-4-hydroxypiperidine

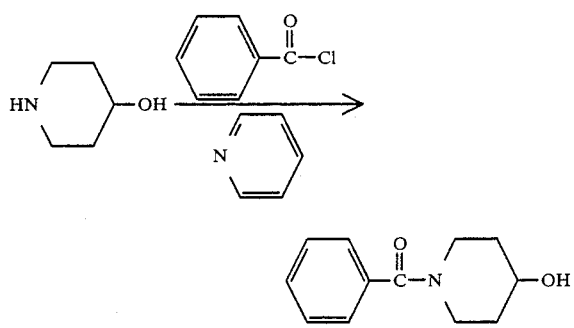

A solution of 73.1 g (520 mmol) of benzoyl chloride in 70 ml of dichloromethane was added dropwise to a solution of 50.0 g (495 mmol) of 4-hydroxypiperidine and 260 ml of pyridine in 260 ml of dichloromethane at 0° to 15° C. The mixture was stirred at room temperature for 3 h and white crystals (pyridine hydrochloride) thus precipitated were filtered out. The filtrate was concentrated and a remaining oil was purified by silica gel column chromatography ($CHCl_3:CH_3OH=95:5$) to give 79.8 g (yield: 79%) of the intended compound:

$^1$H-NMR(90 MHz, CDCl$_3$)δ; 1.20~2.05(4H,m), 2.80~4.30(4H,m), 3.82 (1H,septet like, J=4 Hz), 7.24(5H, s)

(2) Preparation of N-benzoyl-4-piperidine methanesulfonate

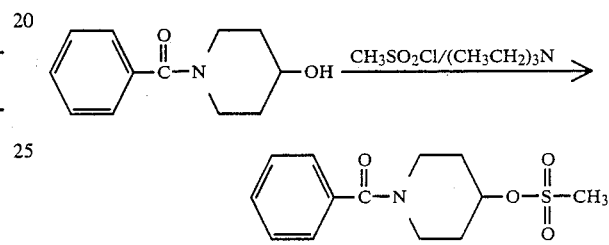

A solution of 53.7 g (467 mmol) of methylsulfonyl chloride in 30 ml of dichloromethane was added dropwise to a solution of 79.8 g (389 mmol) of N-benzoyl-4-hydroxypiperidine obtained in the above step (1) and 47.2 g (467 mmol) of triethylamine in 600 ml of dichloromethane at a temperature of −10° to 10° C. The mixture was stirred at room temperature for 3 h and washed with water and then with a saturated aqueous common salt solution. The organic layer was concentrated to give 102.2 g (yield: 98%) of the intended compound in the form of a colorless oil.

$^1$H-NMR(90 MHz, CDCl$_3$) δ; 1.60~2.20(4H,m), 3.02(3H,s), 3.20~4.00(4H,m), 4.91(1H,m), 7.33 (5H,s)

(3) Preparation of N-benzoyl-4-bromopiperidine

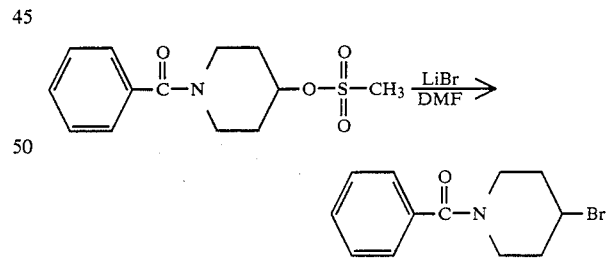

A solution of 13.8 g (159 mmol) of lithium bromide in 150 ml of dimethylformamide was added to a solution of 34.5 g (112 mmol) of N-benzoyl-4-piperidine methanesulfonate obtained in the above step (2) in 100 ml of dimethylformamide (DMF) and the mixture was stirred at 90° C. for 6 h. The mixture was concentrated and water was added to the residue. After extraction with ethyl acetate, the organic layer was concentrated and the residue was purified by silica gel column chromatography to give 16.5 g (yield: 50%) of the intended compound in the form of a light brown oil.

$^1$H-NMR(90 MHz,CDCl$_3$) δ; 1.80~2.36(4H,m), 3.28~4.20(4H,m), 4.41(1H,m), 7.36(5H,s)

(4) Preparation of 4-methanesulfonylaminophenyl disulfide

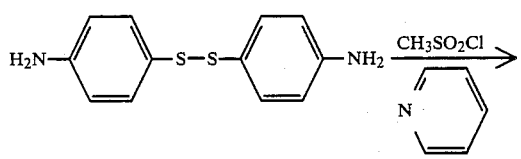

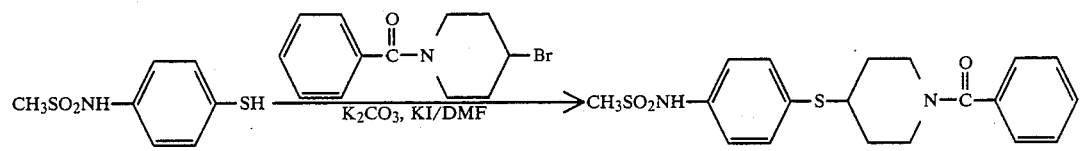

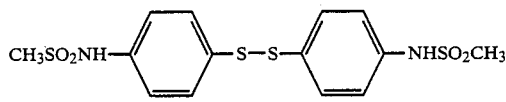

A solution of 22.8 g (199 mmol) of methylsulfonyl chloride in 40 ml of chloroform was added dropwise to a solution of 20.0 g (80.7 mmol) of 4-aminophenyl disulfide and 40 ml of pyridine in 160 ml of chloroform at −10° to 0° C. The mixture was stirred at 0° for 2 H. 80 ml of water was added thereto and the mixture was vigorously stirred. Crystals thus precipitated were collected by filtration to give 32.2 g (yield: 99%) of the intended compound in the form of light red crystals.

M.P. (° C.): 211~212

$^1$H-NMR (90 MHz, DMSO-d$_6$)δ; 2.98 (6H,s), 7.10(4H,d,J=8 Hz), 7.40 (4h,d,J=8 Hz)

(5) Preparation of 4-methylsulfonylaminothiophenol

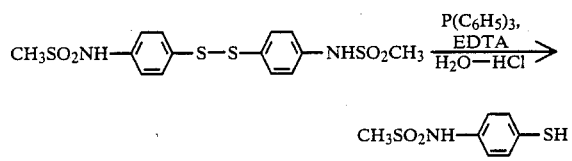

52.9 g (203 mmol) of triphenylphosphine was added to a solution of 41.0 g (102 mmol) of 4-methanesulfonylaminophenyl disulfide obtained in the above step (4), 3.83 g (13.1 mmol) of ethylenediaminetetraacetic acid (EDTA) and 20 ml of 1N hydrochloric acid in a mixture of 400 ml of dioxane with 400 ml of water. The mixture thus obtained was stirred at room temperature for 12 h. After extraction with ethyl acetate, the organic layer was adjusted to a pH of about 11 with a 1N aqueous sodium hydroxide solution After extraction with water, the aqueous layer was washed with a small amount of ether 1N hydrochloric acid was added thereto at 0° C. to adjust the pH to about 3. White crystals thus precipitated were collected by filtration to give 40.7 g (yield: 99%) of the intended compound

M.P. (°C.); 181~182

$^1$H-NMR(90 MHz, DMSO-d$_6$(ε; 2.98 (3H,s), 7.09 (2H,d,J=8), 7.39 (2d,J=8 Hz)

(6) Preparation of N-benzoyl-4-(4-methylsulfonyl-aminophenylthio)-piperidine A solution of 5.60 g (27.6 mmol) of 4-methylsulfonylaminothiophenol obtained in the above step (5) and 7.61 g (55.2 mmol) of potassium carbonate in 100 ml of dimethylformamide was stirred at room temperature for 10 min. 7.40 g (27.6 mmol) of N-benzoyl-4-bromopiperidine prepared in the above step (3) and 9.22 g (55.2 mmol) of potassium iodide were added to the solution and the mixture was stirred at 90° C. for 1.5 h. The mixture was filtered. The filtrate was concentrated and the residue was purified by silica gel column chromatography (CHCl$_3$:CH$_3$H=98:2). The fraction of the intended compound was concentrated to give 8.80 g (yield 80%) of the compound in the form of white crystals.

M.P. (°C.); 184~185

$^1$H-NMR(90 MHz, CDCl$_3$)δ; 1.40~2.10(4H,m), 2.99(3H,s), 2.90~410(5H,m), 7.22(2H,d,J=8 Hz), 7.36 (2H,d,J=8 Hz), 7.36

(7) Preparation of 4(4-methylsulfonylaminophenylthio) piperidine hydrochloride

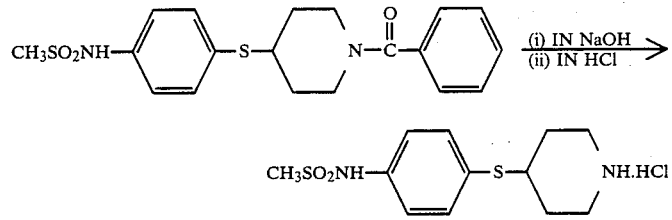

88 ml of a solution of 8.60 g (21.5 mmol) of N-benzoyl-4-(4-methylsulfonylaminophenylthio)piperidine obtained in the above step (6) in a 1N aqueous sodium hydroxide solution was refluxed for 6 h. The reaction solution was cooled. 120 ml of 1N hydrochloric acid was added thereto to acidify the solution to thereby form white crystals. The crystals were collected by filtration and washed with ethanol to give 6.11 g (yield: 88%) of the intended compound.

MASS; (FAB) 287 (MH+)

Elementary analysis:

|  | C | H | N |
| --- | --- | --- | --- |
| Calculated (%) | 44.69 | 5.94 | 8.69 |
| Found (%) | 44.69 | 5.76 | 8.67 |

¹H-NMR (90 MHz, DMSO-d₆)δ; 1.60~2.20(4H,M), 2.70~3.50(5H,m), 3.00(3H,s), 7.17(2H,d,J=8 Hz), 7.40 (2H,d,J=8 Hz), 9.40 (2H,br)

(8) Preparation of 4-(4-methylsulfonylaminophenylthio-1-[2-(3-pyridyl)ethyl]piperidine

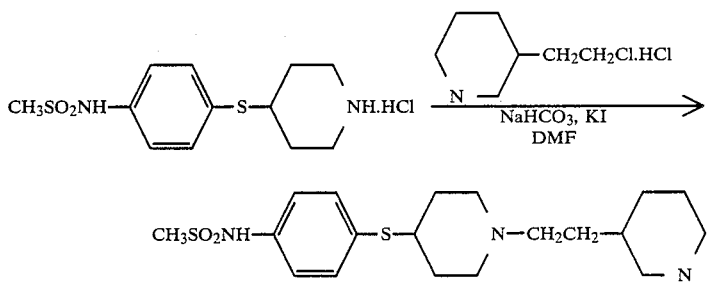

A solution of 4.00 g (12.4 mmol) of 4-(4-methylsulfonylaminophenylthio)piperidine hydrochloride obtained in the above step (7) and 4.17 g (49.6 mmol) of sodium hydrogencarbonate in 40 ml of dimethylformamiide was stirred at 85° C. for 40 min. 4.12 g (24.8 mmol) of potassium iodide and 2.43 g (13.6 mmol) of 2-(3-pyridyl)ethyl chloride hydrochloride prepared by an ordinary method were added to the solution. The mixture was stirred at 85° C. for 1.5 h. The reaction mixture was filtered. The filtrate was concentrated to give a residue, which was purified by silica gel column chromatography (CHCl₃:CH₃OH:NH₄OH=97:3:0.3). The fraction containing the intended compound was concentrated to give a solid residue, which was recrystallized from ethyl acetate to give 1.82 g (yield: 38%) of the intended compound in the form of white crystals.
M.P. (°C.); 126~129
MASS; m/e (EI) 391 (M⁺), 299 (base), 97
Elementary analysis for $C_{19}H_{25}N_3O_2S_2 \cdot 0.5H_2O$:

| | C | H | N |
|---|---|---|---|
| Calculated (%) | 56.97 | 6.54 | 10.49 |
| Found (%) | 56.97 | 6.40 | 10.40 |

¹H-NMR(90 MHz,CDCl₃)δ; 1.50~2.40(4H,m), 2.40~3.20(5H,m), 3.03 (3H,s), 7.08~7.24(3H,M), 7.40 (2H,d,J=8 Hz),7.52 (1H,bred,J=8 Hz), 8.44(2H,m)

EXAMPLE 2

1-[2-(3,4-Dimethoxyphenyl)ethyl]-4-(4-methylsulfonylaminophenylthio)piperidine

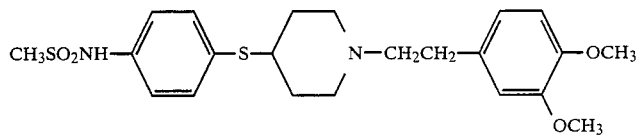

The same procedure as that of Example 1 (1) to (8) was repeated except that 2-(3-pyridyl)ethyl chloride hydrochloride was replaced with 3,4-dimethoxyphenethyl chloride to prepare the intended compound.
M.P. (°C.): 104~106
MASS: (FD) 450(M⁺), 372, 203
Elementary analysis for $C_{22}H_{30}N_2O_4S_2$:

| | C | H | N |
|---|---|---|---|
| Calculated (%) | 58.64 | 6.71 | 6.22 |
| Found (%) | 58.87 | 6.69 | 6.16 |

¹H-NMR (90 MHz, CDCl₃)δ; 1.50~2.30(4H,m), 2.40~3.20(9H,m), 3.01 (3H,s), 3.84(6H,s), 6.74 (3H,M), 7.13(2H,d,J=8 Hz). 7.40 (2H,d,J=8 Hz)

EXAMPLE 3

4--3-Methylsulfonylaminophenylsulfinyl)-1-[2-(3pyridyl)ethyl]piperidine

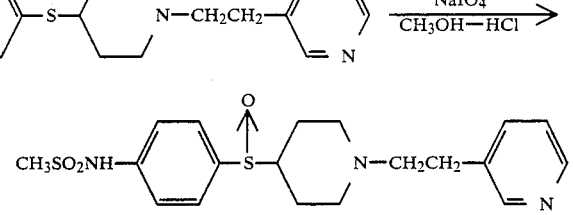

A mixture of 0.50 g (1.28 mmol) of 4-(4-methylsulfonylaminophenylthio)-1-[2-(3-pyridyl)ethyl]piperidine, 0.33 g (1.53 mmol) of sodium periodate, 5 ml of 1N hydrochloric acid and 5 ml of methanol was stirred at room temperature for h. About 5 ml of a 1N sodium hydroxide solution was added thereto to adjust the pH to about 7. After extraction with chloroform, the organic layer was concentrated and the residue was purified by silica gel column chromatography (CHCl₃:CH₃OH: NH$_{OH}$=95:5:0.5). The fraction containing the intended compound was concentrated to give a solid residue, which was recrystallized from ethyl acetate to give a 0.34 g (yield: 64%) of the compound.

M.P. (°C.); 158~159
MASS; m/e (FAB) 408(MH+), 392
Elementary analysis for $C_{19}H_{25}N_3O_3S_2$:

|  | C | H | N |
|---|---|---|---|
| Calculated (%) | 56.00 | 6.18 | 10.31 |
| Found (%) | 55.98 | 6.18 | 10.27 |

¹H-NMR(90MHz,CDCl₃)δ; 1.56~2.30(6H,m), 2.40~3.20(7H,M), 3.07(3H,s), 7.40(1H,dd,J=8 Hz,5 Hzx), 7.30~7.68 (5H,m), 8.44(2H,m)

EXAMPLE 4

1-[2-(3,4-Dimethoxyphenyl)ethyl]-4-(4methylsulfonylaminophenylsulfinyl)piperidine

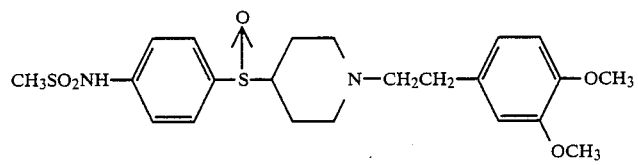

The same procedure as that of Example 3 was repeated except that 1-[2-(3,4-dimethoxyphenyl)ethyl]-(4-methylsulfonylaminophenylthio)piperidine was used to prepare the intended compound.

M.P.(°C.); 128~130
MASS; m/e (FAB) 467(MH+), 451, 248
Elementary analysis for $C_{22}H_{30}N_2O_5S_2$:

|  | C | H | N |
|---|---|---|---|
| Calculated (%) | 56.63 | 6.48 | 6.00 |
| Found (%) | 56.75 | 6.46 | 5.98 |

¹H-NMR(90 MHz,CDCl₃)δ; 1.58~2.30(6H,mn), 2.45~3.20(7H,M), 3.07 (3H,s), 3.84 (6H,s), 6.72 (3H,m), 7.34 (2H,d,J=8 Hz), 7.58 (2H,d,J=8 Hz)

EXAMPLE 5

4-(4-Methylsulfonylaminophenylsulfonyl)piperidine hydrochloride

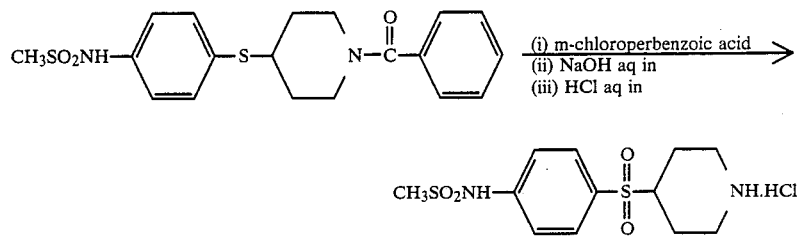

(1)
1-Benzoyl-4-(4-methylsulfonylaminophenylsulfonyl)-piperidine 8.18 g (40.3 mmol) of m-chloroperbenzoic acid was added in portions to a solution of 7.00 g (17.5 mmol) of 1-benzoyl-4-(4-methylsulfonylaminothio)piperidine in 100 ml of dichloromethane and the mixture was stirred at room temperature for 1 h. 20 ml of a 10% aqueous sodium thiosulfate solution was added thereto and the mixture was stirred. Crystals thus precipitated were collected by filtration and washed with water to give the intended compound in the form of white crystals.

(2) 4-(4-Methylsulfonylaminophenylsulfonyl)piperidine hydrochloride

The same procedure as that of Example 1-(7) was repeated except that 1-benzoyl-4-(4-methylsulfonylaminophenylsulfonyl)piperidine obtained in the above step (1) was used to give the intended compound in the form of white crystals.

M.P.(°C.); ca. 273 (dec.)
MASS; m/e (FAB) 319 (MH+), 277, 201(base)
Elementary analysis for $C_{12}H_{18}N_2O_4S_2$.HCl;

|  | C | H | N |
|---|---|---|---|
| Calculated (%) | 40.65 | 5.40 | 7.90 |
| Found (%) | 40.62 | 5.27 | 7.86 |

¹H-NMR (90 MHz, DMSO-d₆) δ; 1.40~2.20 (4H, m), 2.60~3.70 (5H, m), 3.18(3H, s), 7.42(2H, d, J=8 Hz), 7.76 (2H, d, J=8 Hz), 9.70 (2H, br)

EXAMPLE 6

1-[2-(6-Methyl-2-pyridyl)ethyl]-4-(4-methylsulfonylaminophenylsulfonyl)piperidine

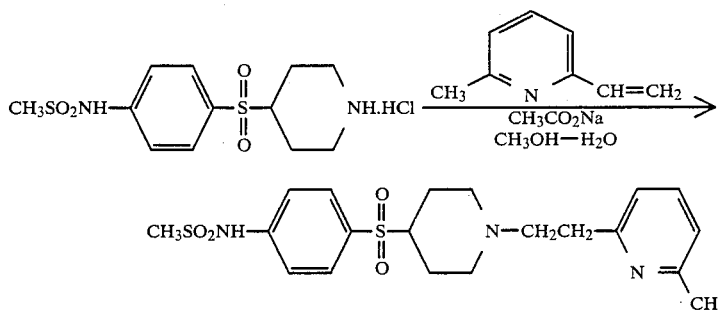

0.60 g (1.86 mmol) of 4-(4-methylsulfonylaminophenylsulfonyl)piperidine hydrochloride obtained in Example 5, 0.44 g (3.72 mmol) of 6-methyl-2-vinylpyridine and 0.31 g of sodium acetate were suspended in 10 ml of a mixture of methanol with water (1:1) and the suspension was refluxed for 2 h. The reaction liquid was filtered and the filtrate was concentrated to give a residue. After extraction with dichloromethane followed by washing with water, the organic layer was concentrated to precipitate white crystals. The crystals were collected by filtration and recrystallized from ethyl acetate to give 0.52 g (yield: 64%) of the intended compound.

M.P.(°C.); 199~200

MASS: m/e (FAB) 438 (MH+), 360, 331, 277

Elementary analysis for $C_{20}H_{27}N_3O_4S_2 \cdot 0.5H_2O$:

|  | C | H | N |
|---|---|---|---|
| Calculated (%) | 53.79 | 6.32 | 9.41 |
| Found (%) | 53.79 | 5.95 | 9.33 |

$^1$H-NMR (90 MHz, DMSO-$d_6$) δ; 1.40~2.40 (6H, m), 2.40~3.50 (7H, m), 2.40 (3H, s), 3.16 (3H, s), 7.03 (2H, d, J=7 Hz), 7.40 (2H, d, J=8 Hz), 7.54 (1H, t, J=7 Hz), 7.78 (2H, d, J=8 Hz).

EXAMPLE 7

1-[2-(2-Chloro-4,5-dimethoxyphenyl)ethyl]-4-(4-methylsulfonylaminophenylsulfonyl)piperidine

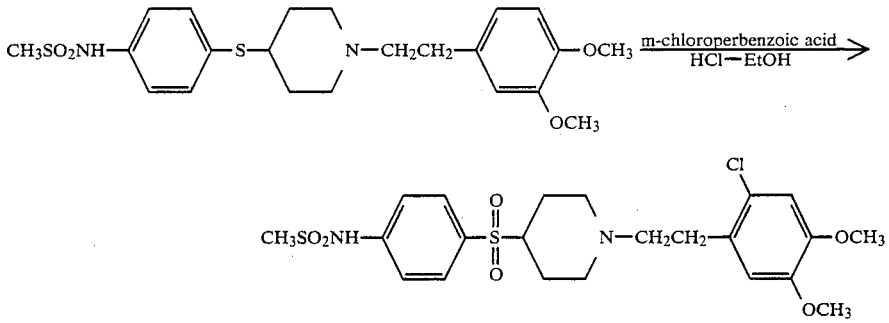

0.61 g (3.0 mmol) of m-chloroperbenzoic acid was added to a mixture of 0.54 g (1.20 mmol) of 1-[2-(3,4-dimethoxyphenyl)ethyl]-4-(4-methylsulfonylaminophenylthio)piperidine, 0.85 ml of 8N hydrochloric acid/ethanol and 15 ml of ethanol and the mixture thus obtained was stirred at room temperature for 1 h. 5 ml of a 10% aqueous sodium thiosulfate solution was added thereto and the mixture was made alkaline with an aqueous sodium hydrogencarbonate solution. After extraction with dichloromethane, the organic layer was concentrated and the residue was purified by silica gel column chromatography. A fraction containing the intended compound was concentrated and the solid residue were recrystallized from ethyl acetate to give 0.34 g (yield: 55%) of the intended compound in the form of white crystals.

M.P.(°C.); 162~164

MASS; m/e (FD) 518(MH+); (FAB) 520(12), 519(46), 518(28), 517(M+, base)

Elementary analysis for $C_{22}H_{29}ClN_2O_6S_2$:

|  | C | H | N |
|---|---|---|---|
| Calculated (%) | 51.10 | 5.65 | 5.42 |
| Found (%) | 50.75 | 5.68 | 5.07 |

$^1$H-NMR (90 MHz, CDCl$_3$-CD$_3$OD) δ; 1.60~2.40 (6H, m), 2.40~4.20 (7H, m), 3.08 (3H, s), 3.80 (6H, s), 6.66 (1H, s), 6.77 (1H, s), 7.32 (2H, d, J=8 Hz), 7.74 (2H, d, J=8 Hz).

EXAMPLES 8 AND 9

The same procedure as that of Example 1-(8) was repeated except that 4-(4-methylsulfonylaminophenylthio)piperidine hydrochloride was replaced with 4-(4-methylsulfonylaminophenylsulfonyl)piperidine hydrochloride to give the compounds shown below.

EXAMPLE 8

4-(4-Methylsulfonylaminophenylsulfonyl)-1-[2-(3-pyridyl)ethyl]piperidine

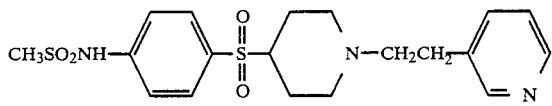

M.P.(°C.); 169~171
MASS; m/e (FAB) 424(M+), 311, 277 201 (base)
Elementary analysis for $C_{19}H_{25}N_3O_4S_2$:

|  | C | H | N |
|---|---|---|---|
| Calculated (%) | 53.88 | 5.95 | 9.92 |
| Found (%) | 53.93 | 5.79 | 9.87 |

$^1$H-NMR (90 MHz), DMSO-$d_6$) δ; 1.40~2.20 (4H, m), 2.40~3.40 (9H, m), 3.15 (3H, s), 7.28 (1H, m), 7.38 (2H, d, J=8 Hz), 7.61 (1H, dt, J=7 Hz, 1 Hz), 7.77 (2H, d, J=8 Hz), 8.37 (2H, m).

EXAMPLE 9

1-[2-(3,4-Dimethoxyphenyl)ethyl]-4-(4-methylsulfonylaminophenylsulfonyl)piperidine

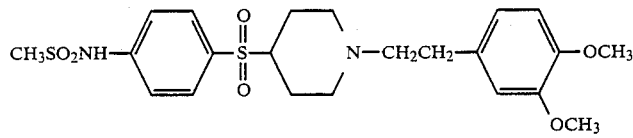

M.P.(°C.); 151~152
MASS; m/e (FAB) 483(M+), 405, 331, 246
Elementary analysis for $C_{22}H_{30}N_2O_6S_2$:

|  | C | H | N |
|---|---|---|---|
| Calculated (%) | 54.75 | 6.27 | 5.80 |
| Found (%) | 54.78 | 6.22 | 5.77 |

$^1$H-NMR (90 MHz), DMSO-$d_6$) δ; 1.30~2.10 (4H, m), 2.20~3.30 (9H, m), 3.14 (3H, s), 3.69 (6H, s), 6.57~6.79 (3H, m), 7.38 (2H, d, J=8 Hz), 7.77 (2H, d, J=8 Hz).

COMPOUND (2)

EXAMPLE 1

N-[4-[N-Methyl-(6-methyl-2-pyridyl)ethylamino]acetylphenyl]methanesulfonamide dioxalate (1) Preparation of N-methyl-N-benzyl(6-methyl-2-pyridyl)ethylamine

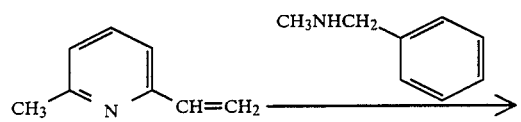

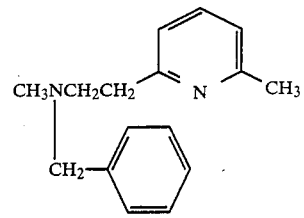

0.5 ml of glacial acetic acid was added to a solution of 10.0 g (84.0 mmol) of 6-methyl-2-vinylpyridine and 10.2 g (84 mmol) of N-methylbenzylamine in 100 ml of a mixture of methanol with water (1:1) and the mixture thus obtained was refluxed for 8 h. The mixture was concentrated and the residue was purified by silica gel column chromatography (chloroform/methanol/aqueous ammonia=97:3:0.3). A fraction containing the intended compound was concentrated to give the compound in the form of an oil.

$^1$H-NMR(90MHz, CDCl$_3$) δ; 2.27 (3H, s), 2.51 (3H, s), 2.64~3.12 (4H, m), 5.55 (2H, s), 6.94 (2H, d, J=8 Hz), 7.25 (5H, s), 7.46 (1H, t, J=8 Hz)

(2) Preparation of N-methyl-(6-methyl-2-pyridyl)ethylamine

N-Methyl-N-benzyl-[(6-methyl-2-pyridyl)-ethyl]amine obtained in the above step (1) was dissolved in a mixture of 200 ml of methanol with 17.2 ml of concentrated hydrochloric acid. 2.0 g of hydrous palladium/carbon (10%) was added to the solution and the catalytic reduction was conducted at 50° C. in an atmosphere of 1-atm hydrogen for 6 h. The catalyst was removed by filtration and the filtrate was completely concentrated. 200 ml of acetonitrile was added to the residue. 20 ml of water was added thereto under violent stirring and then excess powdery sodium hydrogencarbonate was added to the mixture. The mixture was violently stirred for 1 h and then filtered. The filtrate was concentrated. Hot acetonitrile was added to the residue. An insoluble inorganic salt was removed by filtration and the filtrate was again concentrated to give 11.2 g (yield: 87% based on 6-methyl-2-vinylpyridine) of the substantially pure intended compound in the form of crystals.

M.P. (°C.); 88~90
$^1$H-NMR(90 MHz, CDCl$_3$) δ; 2.52 (6H, s), 3.03 (3H, s), 6.98(2H, d, J=8 Hz), 7.48(1H, t, J=8 Hz)

(3) Preparation of N-[4-[N-methyl-(6-methyl-2-pyridyl)ethylamino]acetylphenyl]methanesulfonamide dioxalate

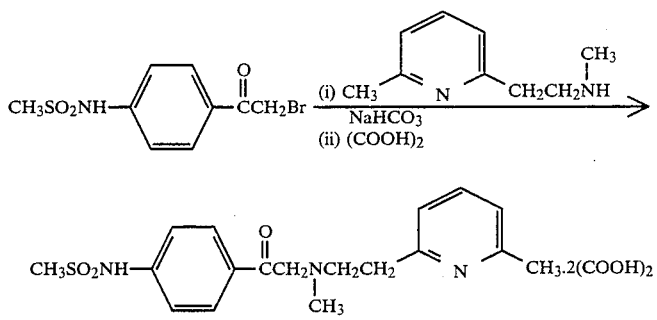

0.35 g (1.73 mmol) of N-[4-(2-bromoacetyl)phenyl]methanesulfonamide was added to a suspension of 0.26 g (1.73 mmol) of N-methyl-(6-methyl-2-pyridyl)-ethylamine obtained in the above step (2) and 0.44 g (5.20 mmol) of sodium hydrogencarbonate in 10 ml of dimethylformamide. The mixture was stirred at room temperature for 5 h. The mixture was filtered. The filtrate was concentrated and the residue was purified by silica gel column chromatography (chloroform/methanol/aqueous ammonia=97:3:0.3). A fraction containing the intended compound was concentrated. 0.18 g (yield: 29%) of the residue was dissolved in ethanol. A solution of 0.09 g of oxalic acid in methanol was added to the solution to give the intended compound in the form of white crystals.

M.P. (°C.); 122~123 m/e (FAB); 362 (MH+)

Elementary analysis for $C_{18}H_{23}N_3O_3S.2(COOH)_2.1.5H_2O$:

|  | C | H | N |
| --- | --- | --- | --- |
| Calculated (%) | 46.48 | 5.31 | 7.39 |
| Found (%) | 46.49 | 4.92 | 7.27 |

$^1$H—NMR (90 MHz, DMSO-$d_5$) δ; 2.46 (3H, s), 2.91 (3H, s), 3.14 (3H, s), 3.00~3.66 (4H, m), 4.93 (2H, s), 7.15 (2H, d, J=8 Hz), 7.33 (2H, d, J=8 Hz), 7.66 (1H, t, J=8 Hz), 7.96 (2H, d, J=8 Hz).

EXAMPLE 2

N-[4-[3-[N-Methyl-(6-methyl-2-pyridyl)ethylamino]-propionyl]phenyl]methanesulfonamide dioxalate ide and the mixture was stirred at room temperature for 4 h. The mixture was filtered. The filtrate was concentrated and the residue was purified by silica gel column chromatography (chloroform/methanol/aqueous ammonia=97:3:0.3). A fraction containing the intended compound was concentrated to give 1.21 g of a residue. A solution of 2 equivalents of oxalic acid in methanol was added to the residue. After recrystallization from ethanol/methanol, 0.90 g (yield: 32%) of the intended compound was obtained in the form of white crystals.

(M.P. (°C.); 142~144 m/e (FAB); 376 (MH+), 163

Elementary analysis for $C_{19}H_{25}N_3O_3S.2(COOH)_2$:

|  | C | H | N |
| --- | --- | --- | --- |
| Calculated (%) | 49.72 | 5.26 | 7.56 |
| Found (%) | 49.72 | 5.24 | 7.36 |

$^1$H-NMR (90 MHz, DMSO-$d_6$)δ; 2.46 (3H, s), 2.80~3.70 (8H, m), 3.13 (3H, s), 7.15 (2H, brd, J=8 Hz), 7.33 (2H, d, J=8 Hz), 7.67 (1H, t, j=8 Hz), 8.001 (2H, d, J=8 Hz).

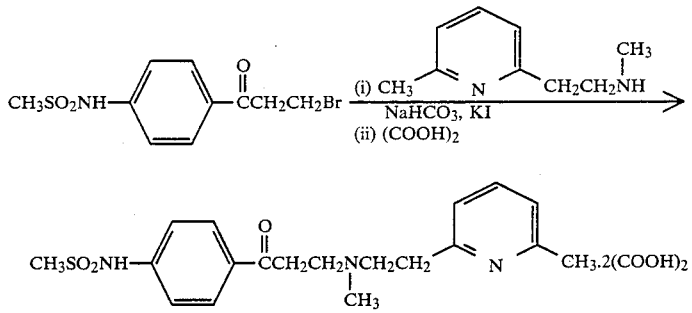

2.04 g (6.67 mmol) of N-[4-(3-bromopropionyl)-phenyl]methanesulfonamide, 1.00 g (6.67 mmol) of N-methyl-(6-methyl-2-pyridyl)ethylamine obtained in Example 1-(2) and 1.68 g (20.0 mmol) of sodium hydrogencarbonate were added to a solution of 2.12 g (6.54 mmol) of potassium iodide in 10 ml of dimethylformam-

EXAMPLE 3

N-[4-[1-Hydroxy-4-[2-(6-methyl-2-pyridyl)ethylamino]-butyl]phenyl]methanesulfonamide oxalate (1) Preparation of N-[2-(6-methyl-2-pyridyl)ethyl]-phthalimide

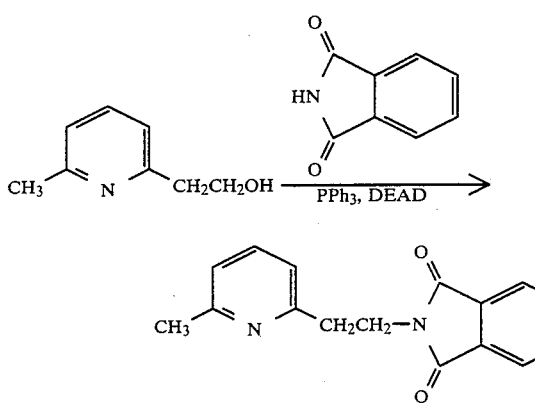

45.6 g (262 mmol) of diethyl azadicarboxylate (DEAD) was added dropwise to a solution of 30.0 g (219 mmol) of 2-(6-methyl-2-pyridyl)ethanol, 38.6 g (262 mmol) of phthalimide and 68.6 g (262 mmol) of triphenylphosphine in 300 ml of tetrahydrofuran at a temperature of 15° to 25° C. The mixture was stirred overnight. Water was added to the mixture. After extraction with ethyl acetate, the organic layer was washed with water After extraction with 2N hydrochloric acid, a 3N sodium hydroxide solution was added to the aqueous layer at 0° C. to make it alkaline. White crystals thus formed were collected by filtration to give 39.04 g (yield: 67%) of the intended compound.

M.P.(°C.); 81~83

$^1$-NMR (90 MHz, CDCl$_3$)δ; 2.42 (3H, s), 3.11 (2H, t, J =7 Hz), 4.06 (2H, t, J=7 Hz), 6.95 (2H, d, J=8 Hz), 7.45 (1H, t, J=8 Hz), 7.62~7.88 (4H, m).

(2) Preparation of 2-(6-methyl-2-pyridyl)ethylamine

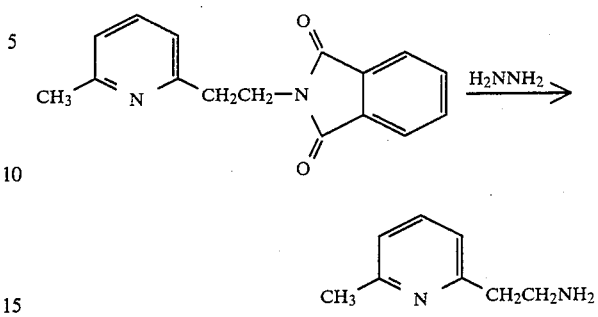

28.5 ml (29.4 g, 586 mmol) of hydrazine monohydrate was added to a solution of 39.0 g (147 mmol) of N-[2-(6-methyl-2-pyridyl)ethyl]phthalimide obtained in the above step (1) in 300 ml of ethanol and the mixture was stirred at room temperature for 1.5 h. The mixture was poured into 300 ml of a saturated aqueous sodium carbonate solution. After extraction with chloroform, the organic layer was concentrated and the oily residue thus obtained was purified by distillation (75° to 80° C./0.01 mmHg). 12.6 g (yield: 63%) of the intended compound was obtained as a colorless oil.

$^1$H-NMR (90 MHz, CDCl$_3$)δ; 2.53 (3H, s), 277~3.18 (4H, m), 6.96 (2H, d, J=8 Hz), 7.48 (1H, t, J=8 Hz).

(3) Preparation of N-[4-[4-[2-(6-methyl-2-pyridyl)-ethylamino]-1,4-dioxobutyl]phenyl]methanesulfonamide

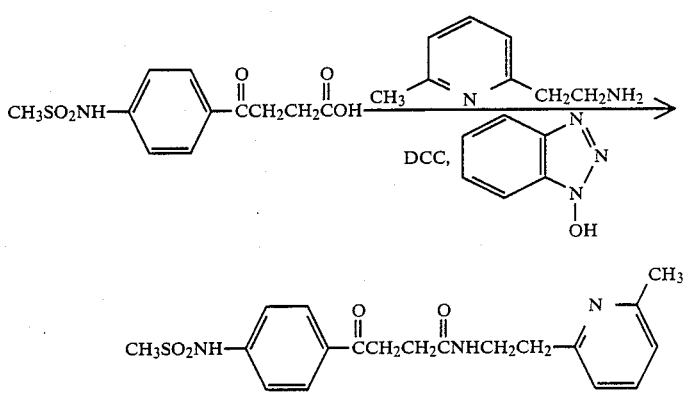

4.76 g (35.3 mmol) of 1-hydroxybenzotriazole and 7.27 g (35.3 mmol) of dicyclohexylcarbodiimide were added to a solution of 7.02 g (29.4 mmol) of 4-(4-methylsulfonylaminophenyl)-4-oxobutyric acid in 60 ml of dimethylformamide at 0° C. and the mixture was stirred at that temperature for 1 h. 4.80 g (35.3 mmol) of 2-(6-methyl-2-pyridyl)ethylamine obtained in the above step (2) was added thereto. The mixture was stirred at room temperature for 12 h and then filtered The filtrate was concentrated. The solid residue thus obtained was washed with a solvent mixture of chloroform/acetic acid/ethanol to give 9.39 g (yield: 89%) of the intended compound in the form of white crystals.

M.P.(°C.); 155~156

$^1$H-NMR (90 MHz, DMSO-d$_6$)δ; 2.35~3.60 (8H, m), 2.43 (3H, s), 3.10 (3H, s), 7.02 (2H, dd, J=7 Hz), 7.27 (2H, d, J=8 Hz), 7.57 (1H, t, J=8 Hz), 7.94 (2H, d, J=8 Hz).

(4) Preparation of N-[4-[1-hydroxy-4-[2-(6-methyl-2-pyridyl)ethylamino]butyl]phenyl]methanesulfonamide oxalate

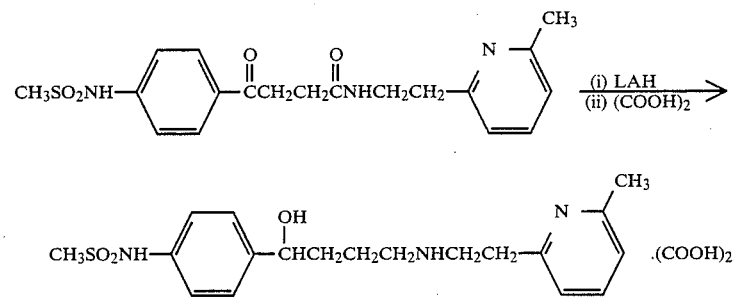

5.38 g (15.1 mmol) of N-[4-[4-[2-(6-methyl-2-pyridyl)ethylamino]-1,4-dioxobutyl]phenyl]methanesulfonamide obtained in the above step (3) was added in small portions to 94.2 ml of 1M solution of lithium aluminum hydride (LAH) in tetrahydrofuran and the mixture was stirred at room temperature for three days. 25 ml of a saturated sodium hydrogencarbonate solution was added dropwise thereto at 0° C. Further 300 ml of ethyl acetate and 100 ml of water were added to the mixture and then concentrated hydrochloric acid was added dropwise thereto to adjust to pH of the mixture to 8.0. After extraction with ethyl acetate, the aqueous layer was further subjected to the extraction with chloroform. The organic layers were combined and concentrated to remove the solvent. The residue was purified by silica gel column chromatography (chloroform/methanol/aqueous ammonia=90:9:1). A fraction containing the intended compound was concentrated to give 3.60 g (yield: 64%) of an oily residue. 0.17 g of this product was weighed out and two equivalents of oxalic acid was added thereto. After recrystallization from ethanol/methanol, 0/18 g of the intended compound was obtained in the form of white crystals.

M.P. (°C.); 137~147 m/e (FAB); 378 (MH+)

Elementary analysis for $C_{19}H_{27}N_3O_3S \cdot (COOH)_2 \cdot H_2O$:

|  | C | H | N |
|---|---|---|---|
| Calculated (%) | 51.94 | 6.43 | 8.65 |
| Found (%) | 51.94 | 6.24 | 8.12 |

$^1$H-NMR (90 MHz, DMSO-d$_6$)δ; 1.50~1.90 (4H, m), 2.15~3.60 (6H, m), 2.43 (3H, s), 2.95 (3H, s), 6.90~7.40 (6H, m), 7.63 (1H, t, J=8 Hz).

EXAMPLE 4

N-[4-[4-[N-Methyl-2-(6-methyl-2-pyridyl)ethylamino]butyryl]-phenyl]methanesulfonamide dioxalate (1) Preparation of N-[4-[1-hydroxy-4-[N-methyl-2-(6-methyl-2-pyridyl)ethylamino]butyl]phenyl]methanesulfonamide

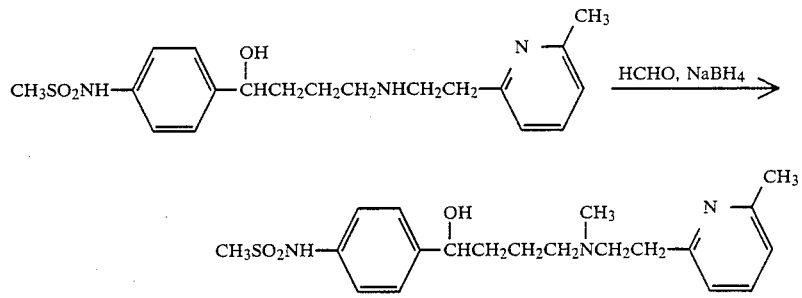

5.19 ml of formalin was added to a solution of 2.12 g (free compound: 6.12 mmol) of N-[4-[1-hydroxy-4-[2-(6-methyl-2-pyridyl)ethylamino]butyl]phenyl]methanesulfonamide obtained in Example 3-(4) in 20 ml of methanol. The mixture was refluxed for 30 min. The mixture was cooled at 0° C. and 0.81 g of sodium borohydride was added in small portions thereto. The mixture was stirred at 0° C. for 20 min. 36 ml of 1N hydrochloric acid was added thereto to acidify it. The solution thus obtained was poured into 100 ml of a saturated sodium hydrogencarbonate solution. After extraction with dichloromethane, the organic layer was concentrated to give 2.16 g (yield: 94%) of the intended compound.

$^1$H-NMR(90 MHz, CDCl$_3$)δ; 1.50~2.00 (4H, m), 2.30~3.12 (6H, m), 2.34 (3H, s), 2.51 (3H, ss), 2.91 (3H, s), 4.53 (1H, m), 6.98 (2H, d, J=8 Hz), 7.00 ~7.32 (4H, m), 7.48 (1H, t, J=8 Hz).

(2) Preparation of
N-[4-[4-[N-methyl-2-(6-methyl-2-pyridyl)ethylamino]-butyryl]phenyl]methanesulfonamide dioxalate

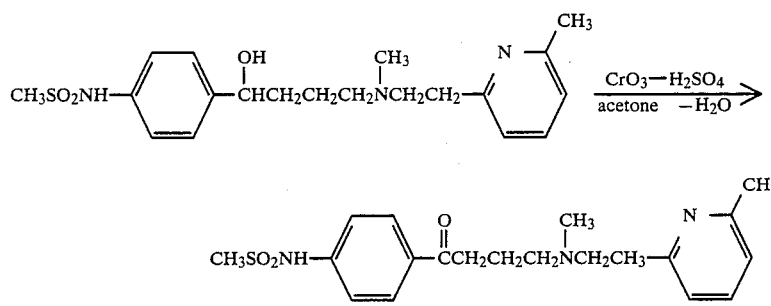

0.42 ml of Jones reagent was added to a solution of 0.10 g (0.27 mmol) of N-[4-[1-hydroxy-4-[N-methyl-2-(6-methyl-2-pyridyl)ethylamino]butyl]phenyl]methanesulfonamide obtained in the above step (1) in 6 ml of acetone/water (1:1). The mixture was stirred at room temperature for 5 h. 1 ml of 2-propanol was added thereto and the mixture was poured into 50 ml of a saturated sodium hydrogencarbonate solution. After extraction with dichloromethane, the organic layer was concentrated to obtain 0.10 g of a residue. Two equivalents of oxalic acid was added to the residue. After recrystallization from a mixture of methanol and ethanol, 0.06 g (yield: 40%) of the intended compound was obtained.

M.P.(°C.); 142~151
m/e (FAB); 390 (MH+)
Elementary analysis for $C_{20}H_{27}N_3O_3S \cdot 2(COOH)_2$:

|  | C | H | N |
|---|---|---|---|
| Calculated (%) | 50.61 | 5.49 | 7.38 |
| Found (%) | 50.61 | 5.74 | 7.26 |

$^1$H-NMR (90 MHz, DMSO-d$_6$)δ; 1.80~2.20 (2H, m), 2.46 (3H, s), 2.85 (3H, s), 3.11 (3H, s), 2.80~3.60 (8H, m), 7.14 (2H, d, J=8 Hz), 7.29 (2H, d, J=8 Hz), 7.64 (1H, t, J=8 Hz), 7.95 (2H, d, J=8 Hz).

EXAMPLE 5

N-[4-[4-[N-Ethyl-2-(6-methyl-2-pyridyl)ethylamino]-butyryl]phenyl]methanesulfonamide dioxalate (1) Preparation of
N-[4-[1-hydroxy-4-[N-ethyl-2-(6-methyl-2-pyridyl)ethylamino]butyl]phenyl]methanesulfonamide

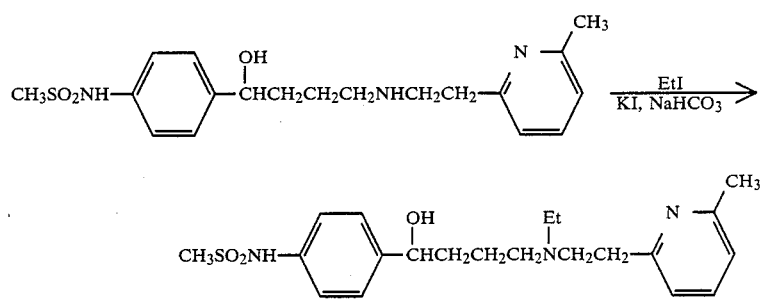

0.24 ml 3.04 mmol) of ethyl iodide was added to a suspension of 1.0 g (2.77 mmol) of N-[4-[1-hydroxy-4-[2-(6-methyl-2-pyridyl)ethylamino]butyl]phenyl]methanesulfonamide prepared in Example 3-(4) and 0.70 g (8.31 mmol) of sodium hydrogencarbonate in 15 ml of dimethylformamide. The mixture was stirred at 50° C. for 2 h and then filtered. The filtrate was concentrated to give a residue, which was purified by silica gel column chromatography (chloroform/methanol/aqueous ammonia=97:3:0.3). 0.96 g (yield: 89%) of the intended compound was obtained in the form of a colorless oil.

(2) Preparation of
N-[4-[4-[N-ethyl-2-(6-methyl-2-pyridyl)ethylamino]-butyryl]phenyl]methanesulfonamide

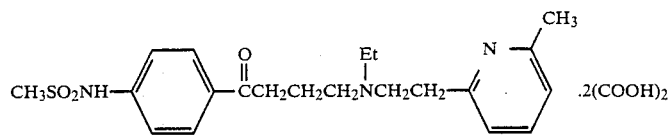

The same procedure as that of Example 4-(2) was repeated except that N-[4-[1-hydroxy-4-[N-methyl-2-(6-methyl-2-pyridyl)ethylamino]butyl]phenyl]methanesulfonamide was replaced with N-[4-[1-hydroxy-4-[N-ethyl-2-(6-methyl-2-pyridyl)ethylamino]butyl]phenyl]methanesulfonamide obtained in the above step (1).

M.P.(°C.); 145~148
m/e (FAB); 404 (MH+)
Elementary analysis for $C_{21}H_{hd 29}N_3O_3S \cdot 2(COOH)_2$:

|  | C | H | N |
|---|---|---|---|
| Calculated (%) | 51.45 | 5.70 | 7.20 |
| Found (%) | 51.40 | 5.67 | 6.97 |

¹H-NMR(90 MHz, DMSO-d₆)δ; 1.26 (3H, t, J=7 Hz), 0.80~1.20 (2H, m), 2.46 (3H, s), 2.95~3.65 (10H, m), 3.11 (3H, s), 7.16 (2H, brd, J=8 Hz), 7.30 (2H, d, J=8 Hz), 7.66 (1H, t, J=8 Hz), 7.95 (2H, d, j=8 Hz).

EXAMPLE 6

The following compounds were prepared in the same manner as that of Example 3 or 4 except that 4-(4-methylsulfonylaminophenyl)-4-oxobutyric acid used as the starting material was replaced with 5-(4-methylsulfonylaminophenyl)-5-oxopentanoic acid:

(1) N-[4-[5-[N-methyl-2-(6-methyl-2-pyridyl)ethylamino]-1,5-dioxopentyl]phenyl]methanesulfonamide

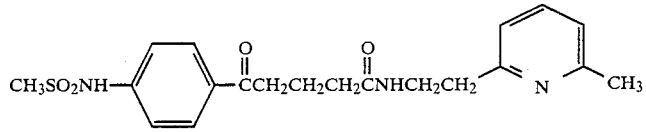

M.P. (°C.)130~131

¹H-NMR (90 MHz, DMSO-d₆)δ; 1.84~2.26 (4H, m), 2.42 (3H, s), 2.60~3.00 (4H, m), 3.10 (3H, s), 3.20~3.32 (2H, m), 7.01 (2H, d, J=8 Hz), 7.28 (2H, d, J=8 Hz), 7.54 (2H, d, J=8 Hz), 7.91 (2H,d, J=8 Hz).

(2) N-[4-[1-hydroxy5-[2-(6-methyl-2-pyridyl)-ethylamino]pentyl]phenyl]methanesulfonamide

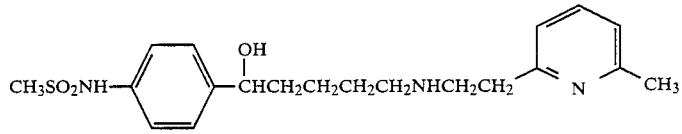

¹H-NMR (90 MHz, CDCl₃)δ; 1.10~1.80 (6H, m), 2.50 (3H, s), 2.66 (2H, m), 2.94 (7H, s), 4.58 (1H, t, J=7 Hz), 6.96 (2H, dd, J=8 Hz, 3 Hz), 7.21 (4H, m), 7.48 (1H, t, J=8 Hz).

(3) N-[4-[1-hydroxy-5-[2-(6-methyl-2-pyridyl)-ethylamino]pentyl]phenyl]methanesulfonamide

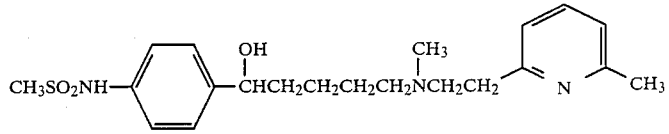

¹H-NMR (90 MHz, CDCl₃)δ; 1.15~1.80 (6H, m), 2.18~3.03 (6H, m), 2.26 (3H, s), 2.49 (3H, s), 2.96 (3H, s), 4.60 (1H, t, J=7 Hz), 6.94 (2H, d, J=8 Hz), 7.23 (4H, m), 7.47 (1H, t, J=8 Hz).

(4) N- 4-[5-[N-methyl-2-(6-methyl-2-pyridyl)-ethylamino]valeryl]phenyl]methanesulfonamide dioxalate

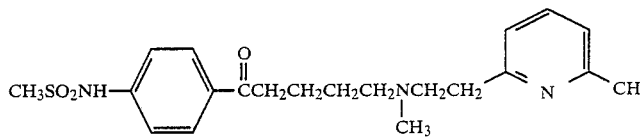

M.P. (°C.); 149~151
m/e (FAB); 404 (MH⁺)
Elementary analysis for C₂₁H₂₉N₃O₃S.2 (COOH)₂:

|  | C | H | N |
|---|---|---|---|
| Calculated (%) | 51.45 | 5.70 | 7.20 |
| Found (%) | 51.24 | 5.56 | 7.06 |

¹H-NMR (90 MHz, DMSO-d₆)δ; 1.50~2.20(4H, m), 2.45 (3H, s), 2.82 (3H, s), 2.70~3.60 (8H, m), 3.10 (3H, s), 7.15 (2H, d, J=8 Hz), 7.29 (2H, d, J=8 Hz), 7.65 l(1H, t, J=8 Hz), 7.94 (2H, d, J=8 Hz).

EXAMPLES 7 to 13

Compounds shown in Table 2 prepared from corresponding starting materials in the same manner as that of Example 2

TABLE 2

| Ex. No. | Y | structure | M.P. (°C.) | m/e | Mol. form. | Element. anal. Upper: calcd. (%) Lower: found (%) C | H | N | $^1$H-NMR (90 MHz) |
|---|---|---|---|---|---|---|---|---|---|
| 7 | —(CH$_2$)$_2$— | 3-OCH$_3$ phenyl; CH$_3$SO$_2$NH–C$_6$H$_4$–C(O)CH$_2$CH$_2$NH–Y | 166~167 | (FD) 377(MH$^+$) | C$_{19}$H$_{24}$N$_2$O$_4$S.HCl | 55.27 55.11 | 6.10 6.09 | 6.78 6.76 | (DMSO-d$_6$) δ: 2.65~3.85(8H, m), 3.12(3H, s), 3.74(3H, s), 6.83 (3H, m), 7.25(1H, t, J=8Hz), 7.33(2H, d, J=8Hz), 7.96(2H, d, J=8Hz), 9.20(2H, br) |
| 8 | —(CH$_2$)$_2$— | 4-OCH$_3$ phenyl | 122~124 | (FD) 377(MH$^+$) | C$_{19}$H$_{24}$N$_2$O$_4$S.O.7H$_2$O | 58.65 58.62 | 6.58 6.34 | 7.20 7.12 | (DMSO-d$_6$) δ: 2.60~3.34(8H, m), 3.02(3H, s), 3.71(3H, s), 6.82 (2H, d, J=8Hz), 7.12(2H, d, J=8Hz), 7.19(2H, d, J=8 Hz), 7.88(2H, d, J=8Hz) |
| 9 | —(CH$_2$)$_2$— | 2,3-diOCH$_3$ phenyl | 139~141 | (FD) 407(MH$^+$) | C$_{20}$H$_{26}$N$_2$O$_5$S.0.9H$_2$O | 56.82 56.86 | 6.62 6.24 | 6.62 6.49 | (DMSO-d$_6$) δ: 2.50~3.34(8H, m), 3.03(3H, s), 3.71(3H, s), 3.73 (3H, s), 6.77(3H, m), 7.20(2H, d, J=8Hz), 7.89(2H, d, J=8Hz) |
| 10 | —(CH$_2$)$_2$— | phenyl; CH$_3$SO$_2$NH–C$_6$H$_4$–C(O)CH$_2$CH$_2$N(CH$_3$)–Y | 144~146 | (FD) 361(MH$^+$) | C$_{19}$H$_{24}$N$_2$O$_3$S.HCl | 57.49 57.60 | 6.35 6.30 | 7.06 7.04 | (DMSO-d$_6$) δ: 2.80~3.64(8H, m), 2.86(3H, s), 3.12(3H, s), 7.31 (5H, s), 7.33(2H, d, J=8Hz), 8.01(2H, d, J=8Hz) |
| 11 | —(CH$_2$)$_2$— | 3,4-diOCH$_3$ phenyl | 159~161 | (FD) 421(MH$^+$) | C$_{21}$H$_{28}$N$_2$O$_5$S.HCl | 55.19 54.83 | 6.40 6.30 | 6.13 6.04 | (DMSO-d$_6$) δ: 2.80~3.82(8H, m), 2.84(3H, s), 3.12(3H, s), 3.71 (3H, s), 3.75(3H, s), 6.86(3H, s), 7.32(2H, d, J=8 Hz), 7.99(2H, d, J=8Hz) |

TABLE 2-continued

| Ex. No. | Y | M.P. (°C.) | m/e | Mol. form. | Element. anal. Upper: calcd. (%) Lower: found (%) C | H | N | $^1$H-NMR (90 MHz) |
|---|---|---|---|---|---|---|---|---|
| 12 | —CH$_2$—C$_6$H$_5$ | 161~162 | (FD) 347(MH$^+$) | C$_{18}$H$_{22}$N$_2$O$_3$S.HCl | 56.46 / 56.37 | 6.05 / 6.03 | 7.32 / 7.29 | (DMSO-d$_6$) δ: 3.30~3.80(4H, m), 2.69(3H, brs), 3.12(3H, s), 4.36(2H, br), 7.33(2H, d, J=8Hz), 7.40~7.80(5H, m), 7.99(2H, d, J=8Hz) |
| 13 | 4-phenylpiperidinyl | 216~219 | (FD) 387(MH$^+$) | C$_{21}$H$_{26}$N$_2$O$_3$S.HCl.0.3H$_2$O | 58.88 / 58.93 | 6.49 / 6.54 | 6.54 / 6.54 | (DMSO-d$_6$) δ: 1.80~2.40(4H, m), 2.60~3.90(9H, m), 3.12(3H, s), 7.33(2H, d, J=8Hz), 7.28(5H, m), 8.00(2H, d, J=8Hz) |

CH$_3$SO$_2$NH—C$_6$H$_4$—C(=O)CH$_2$CH$_2$—Y

COMPOUND (3)

EXAMPLE 1

Preparation of N-[4-[2-hydroxy-1-[4-(4-fluorobenzoyl)piperidyl]ethyl]phenyl]methanesulfonamide hydrochloride (1) N-[4-(2-bromo-1-hydroxyethyl)phenyl]methanesulfonamide

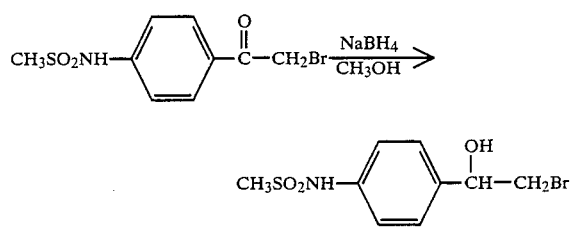

20.0 g (61.0 mmol) of N-[4-(2-bromoacetyl)phenyl]methanesulfonamide was suspended in 240 ml of methanol. 2.84 g of sodium borohydride was added in three portions at invervals of 5 min to the suspension cooled at −20° C. The mixture was stirred at −20° C. for 2 h. Concentrated hydrochloric acid was added dropwise to the mixture to acidify it. 300 ml of water and 500 ml of chloroform were added thereto. After extraction with chloroform, the organic layer was concentrated and a solid residue thus obtained was recrystallized from ether to give 16.4 g (yield: 82%) of the intended compound in the form of white crystals

M.P. (°C.); 91~93

$^1$H-NMR(90 MHz, DMSO-d$_6$)δ; 2.96 (3H, s), 3.61 (2H, m), 4.75 (1H, q like, J=7 Hz), 5.78 (1H, d, J=5 Hz), 7.15 (2H, D, J=8 Hz), 7.35 (2H, d, J=8 Hz), 9.70 (1H, brs).

(2) N-[4 [2-hydroxy-1-[4-(4-fluorobenzoyl) piperidyl]ethyl]phenyl]methanesulfonamide hydrochloride:

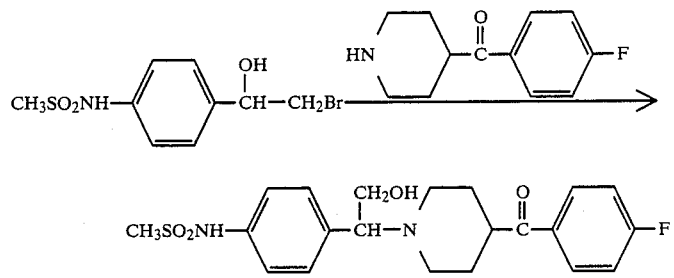

A solution of 4.00 g (16.4 mmol) of 4-(4-fluorobenzoyl)piperidine hydrochloride and 11.3 g (81.9 mmol) of potassium carbonate in 100 ml of dimethylformaide was stirred at room temperature for 30 min. 4.82 g (16.4 mmol) of N-[4-(2-bromo-1-hydroxyethyl)phenyl]methanesulfonamide prepared in the above step (1) and 2.72 g (16.4 mmol) of potassium iodide were added thereto. The mixture was stirred at 90° C. for 3 h and then filtered. The filtrate was concentrated and the residue thus obtained was purified by silica gel column chromatography (chloroform/methanol=97:3). A fraction containing the intended compound was concentrated. An excess hydrochloric acid/ethanol solution was added to the residue. After recrystallization from ethanol/2-propanol 2.41 g of the intended compound was obtained in the form of white crystals.

M.P. (°C.); 199~202

MASS; m/e 389 (M$^+$−H$_2$O)

Elementary analysis for C$_{21}$H$_{25}$FN$_2$O$_4$S.HCl:

|  | C | H | N |
|---|---|---|---|
| Calculated (%) | 55.20 | 5.73 | 6.13 |
| Found (%) | 55.22 | 5.97 | 5.94 |

$^1$H-NMR (90 MHz, DMSO-d$_6$)δ; 1.70~2.40 (4H, m), 2.60~3.50 (8H, m), 3.04 (3H, s), 710~7.70 (6H, m), 8.00 (2H, m).

EXAMPLES 2 to 5

Compounds shown in Table 3 were obtained from corresponding compounds (IV) in the same manner as that of Example 1.

TABLE 3

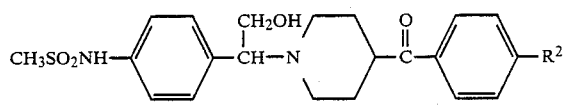

| Ex. No. | R$^2$ | M.P. (°C.) | m/e | Mol. form. | Element anal. Upper: calcd. (%) Lower: found (%) | | | $^1$H-NMR (90 MHz) |
|---|---|---|---|---|---|---|---|---|
|  |  |  |  |  | C | H | N |  |
| 2 | —H | 192~193 | (FAB) 403(MH$^+$) | C$_{21}$H$_{26}$N$_2$O$_4$S | 62.66 62.50 | 6.51 6.62 | 6.96 6.68 | (DMSO-d$_6$) δ: 1.60~2.00(4H, m), 2.00~4.10(8H, m), 2.96(3H, s), 7.26(4H, m), 7.52(3H, m), 7.92(2H,dd,J=8Hz,2Hz) |
| 3 | —CH$_3$ | 187~188 | (FAB) 417(MH$^+$) | C$_{22}$H$_{28}$N$_2$O$_4$S | 63.44 63.35 | 6.78 6.86 | 6.72 6.46 | (DMSO-d$_6$) δ: 1.60~1.90(4H, m), 1.90~3.55(5H, m), 2.99(3H, s), 3.68(2H, brd,J=7Hz), 4.25(1H, br), 7.19(4H, m), 7.28(2H, d, J=8hz), 7.83(2H, d, J=8Hz) |
| 4 | —Cl | 198~200 | (FD) 437(MH$^+$) | C$_{21}$H$_{25}$ClN$_2$O$_4$S.0.2H$_2$O | 57.25 57.28 | 5.81 5.70 | 6.36 6.32 | (DMSO-d$_6$) δ: 1.50~1.90(4H, m), 1.90~4.40(8H, m), 2.99(3H, s), |

TABLE 3-continued

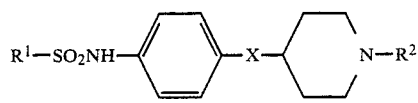

| Ex. No. | R² | M.P. (°C.) | m/e | Mol. form. | Element anal. Upper: calcd. (%) Lower: found (%) | | | ¹H-NMR (90 MHz) |
|---|---|---|---|---|---|---|---|---|
| | | | | | C | H | N | |
| 5 | —OH | 191~192 | (FAB) 419(M⁺) | C₂₁H₂₅N₂O₅S | 60.27 60.25 | 6.26 6.32 | 6.69 6.54 | 7.19(4H, m), 7.53(2H, d, J= 8Hz), 7.95(2H, d, J=8Hz) (DMSO-d₆) δ: 6.80(2H, d, J=8Hz), 7.19(4H, m), 7.81(2H, d, J=8Hz) |

We claim:

1. A compound having the formula

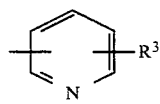

in which R¹ is lower alkyl;
X is —S—, — SO— or —SO₂—; and
R² is hydrogen or —(CH₂)ₙ—Y, wherein n is an integer of 1 to 5, and Y is (1) phenyl, (2) phenyl substituted with from 1 to 3 substituents selected from the group consisting of alkyl having 1 to 6 carbon atoms, alkoxy having from 1 to 6 carbon atoms and halogen or (3)

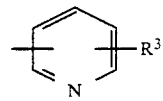

in which R³ is hydrogen, lower alkyl, lower alkoxy, cyano, hydroxyl or halogen or a pharmacologically acceptable salt thereof.

2. A compound as claimed in claim 1 and a in which X is —SO—.

3. A pharmaceutical composition which comprises a pharmaceutically effective amount of a compound as defined in claim 1 and a pharmacologically acceptable carrier.

4. A method of treating a patient afflicted with arrhythmia which comprises administering to the patient a therapeutically effective amount of a compound as defined in claim 1

5. A compound as claimed in claim 1 in which X is —SO₂—.

6. A compound as claimed in claim 1 in which X is —S—.

7. A compound as claimed in claim 1 in which R² is hydrogen.

8. A compound as claimed in claim 1 in which R² is —(CH₂)ₙ—Y.

9. A compound as claimed in claim 8 in which Y is phenyl or phenyl substituted with from 1 to 3 substituents selected from the group consisting of alkyl having 1 to 6 carbon atoms, alkoxy having from 1 to 6 carbon atoms and halogen.

10. A compound as claimed in claim 9 in which n is an integer of 1 or 2.

11. A compound as claimed in claim 8 in which Y is

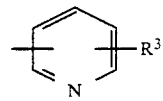

wherein R³ is hydrogen, lower alkyl, lower alkoxy, cyano, hydroxyl or halogen.

12. A compound as claimed in claim 1 in which R² is pyridylmethyl, pyridylethyl, methylpyridylmethyl or methylpyridylethyl.

13. A compound as claimed in claim 1 having the formula

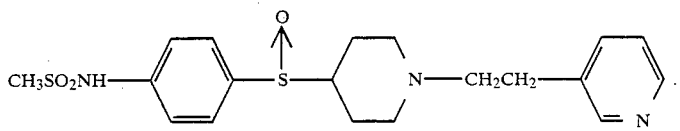

14. A compound as claimed in claim 1 having the formula

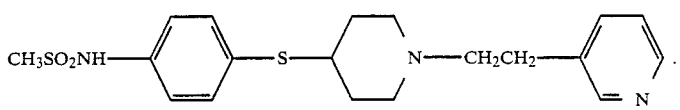

15. A compound as claimed in claim 1 having the formula

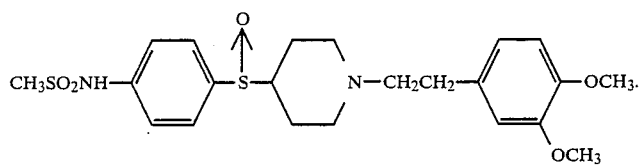
16. A compound as claimed in claim 1 having the formula
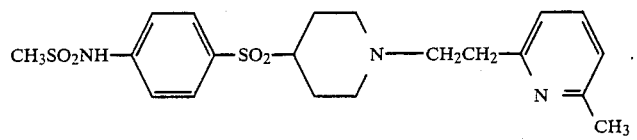
17. A compound as claimed in claim 1 having the formula
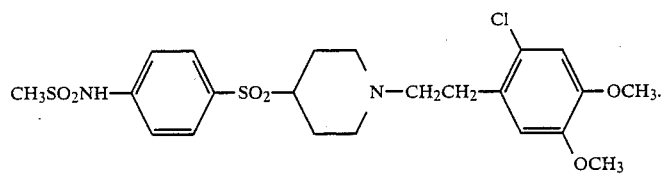
18. A compound as claimed in claim 1 having the formula
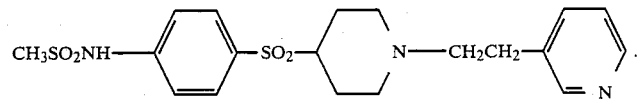
19. A compound as claimed in claim 1 having the formula
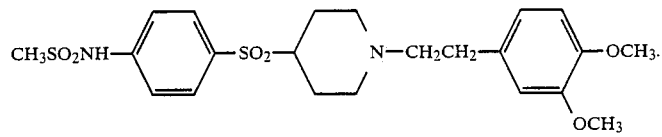
20. A compound as claimed in claim 1 having the formula
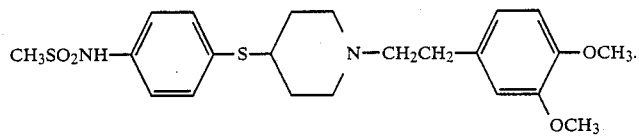
* * * * *

UNITED STATES PATENT AND TRADEMARK OFFICE
CERTIFICATE OF CORRECTION

PATENT NO. : 4,977,165

DATED : December 11, 1990

INVENTOR(S) : Hitoshi OINUMA et al

It is certified that error appears in the above-identified patent and that said Letters Patent is hereby corrected as shown below:

ON TITLE PAGE: item [54], change "DERIVATIVE" to ---DERIVATIVES---.

On the face sheet, item [75], add to the list of inventors the following:

---Yoshiharu Daiku, Tsukuba; Kohei Sawada, Tsukuba; and Kenichi Nomoto, Tsuchiura,---.

Column 47, line 37; after the formula insert a comma.

line 41; after "halogen" insert a comma.

line 43; delete "and a".

Signed and Sealed this

Fourth Day of August, 1992

*Attest:*

DOUGLAS B. COMER

*Attesting Officer*   Acting Commissioner of Patents and Trademarks